United States Patent
Fiedler et al.

(10) Patent No.: US 11,548,929 B2
(45) Date of Patent: Jan. 10, 2023

(54) FC BINDING PROTEINS WITH CYSTEINE IN THE C-TERMINAL HELICAL REGION

(71) Applicant: Repligen Corporation, Waltham, MA (US)

(72) Inventors: Erik Fiedler, Halle/Saale (DE); Ulrich Haupts, Halle/Saale (DE)

(73) Assignee: Repligen Corporation, Waltham, MA (US)

( * ) Notice: Subject to any disclaimer, the term of this patent is extended or adjusted under 35 U.S.C. 154(b) by 55 days.

(21) Appl. No.: 16/965,833

(22) PCT Filed: Jan. 28, 2019

(86) PCT No.: PCT/US2019/015433
§ 371 (c)(1),
(2) Date: Jul. 29, 2020

(87) PCT Pub. No.: WO2019/152318
PCT Pub. Date: Aug. 8, 2019

(65) Prior Publication Data
US 2021/0054044 A1  Feb. 25, 2021

(30) Foreign Application Priority Data
Feb. 1, 2018 (EP) .................... 18154731

(51) Int. Cl.
*A61K 38/00* (2006.01)
*C07K 14/735* (2006.01)
*C07K 1/14* (2006.01)

(52) U.S. Cl.
CPC .......... *C07K 14/70535* (2013.01); *C07K 1/14* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 8,674,073 | B2 | 3/2014 | Majima et al. |
| 2010/0063256 | A1 | 3/2010 | Spector |
| 2014/0107315 | A1 | 4/2014 | Yoshida et al. |
| 2015/0056240 | A1 | 2/2015 | Schneewind et al. |

FOREIGN PATENT DOCUMENTS

| | | |
|---|---|---|
| CN | 101522278 A | 9/2009 |
| CN | 105377880 A | 3/2016 |
| EP | 2557157 A1 | 2/2013 |
| WO | 2015097041 A1 | 7/2015 |
| WO | 2016079034 A1 | 5/2016 |
| WO | 2018029157 A1 | 2/2018 |
| WO | 2019030156 A1 | 2/2019 |
| WO | 2019152318 A1 | 8/2019 |

OTHER PUBLICATIONS

International Search Report and Written Opinion dated Jul. 18, 2019 for PCT/US2019/15433.

*Primary Examiner* — Thomas S Heard
(74) *Attorney, Agent, or Firm* — KDB Firm PLLC

(57) ABSTRACT

The present invention relates to Fc binding proteins comprising one or more domains with Cysteine in the C-terminal helical region. The invention further relates to affinity matrices comprising the Fc binding proteins of the invention. The invention also relates to a use of these Fc binding proteins or affinity matrices for affinity purification of immunoglobulins and to methods of affinity purification using the Fc binding proteins of the invention.

15 Claims, 5 Drawing Sheets
Specification includes a Sequence Listing.

FIG. 1A

| Fc BINDING DOMAIN (SEQ ID NO: 2) | | | | | | | | | | | | | | | | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 |
| I | A | A | K | H | D | K | D | Q | Q | A | A | F | Y | E | I | L | L | H | L | P | N | L | T | E | D | Q | R | N | A | F | I | Q | S | L | R | D | D | P | S | V | S | L | E | T | L | G | E | A | K | K | L | N | D | A | Q | A | P |
| | D | | N | Q | F | | E | A | | S | | | | | E | | | | | | | | | E | | | | | | | | | | I | | | | | T | | | C | C | | L | C | C | Q | | | | N | D | | | | |
| | | | | | | E | | | | E | | | | | | | | | | | | | | | | | | | | | Q | | | | | | | | Q | | | S | V | | A | | | | | | | E | S | | | | |
| | | | | | | | | | | T | | | | | | | | | | | | | | | | | | | | | | | | | | | | | | | | | | | | | | | | | | C | | | | | K |

SEQUENCE LISTING

```
<160> NUMBER OF SEQ ID NOS: 95

<210> SEQ ID NO 1
<211> LENGTH: 58
<212> TYPE: PRT
<213> ORGANISM: Artificial Sequence
<220> FEATURE:
<223> OTHER INFORMATION: consensus sequence 1
<220> FEATURE:
<221> NAME/KEY: variant
<222> LOCATION: (1)..(1)
<223> OTHER INFORMATION: may be replaced by A, N, Q, V, or deleted
<220> FEATURE:
<221> NAME/KEY: variant
<222> LOCATION: (2)..(2)
<223> OTHER INFORMATION: may be replaced by D or Q, or deleted
<220> FEATURE:
<221> NAME/KEY: variant
<222> LOCATION: (3)..(3)
<223> OTHER INFORMATION: may be replaced by N, or deleted
<220> FEATURE:
<221> NAME/KEY: variant
<222> LOCATION: (4)..(4)
<223> OTHER INFORMATION: may be replaced by Q or N, or deleted
<220> FEATURE:
<221> NAME/KEY: variant
<222> LOCATION: (5)..(5)
<223> OTHER INFORMATION: may be replaced by F, or deleted
<220> FEATURE:
<221> NAME/KEY: variant
<222> LOCATION: (6)..(6)
<223> OTHER INFORMATION: may be replaced by N, or deleted
<220> FEATURE:
<221> NAME/KEY: variant
<222> LOCATION: (7)..(7)
<223> OTHER INFORMATION: may be replaced by E
<220> FEATURE:
<221> NAME/KEY: variant
<222> LOCATION: (8)..(8)
<223> OTHER INFORMATION: may be replaced by A or E
<220> FEATURE:
<221> NAME/KEY: variant
<222> LOCATION: (11)..(11)
<223> OTHER INFORMATION: may be replaced by S, N, I ,or E
<220> FEATURE:
<221> NAME/KEY: variant
<222> LOCATION: (15)..(15)
<223> OTHER INFORMATION: may be replaced by Q
<220> FEATURE:
<221> NAME/KEY: variant
<222> LOCATION: (16)..(16)
<223> OTHER INFORMATION: may be replaced by V
<220> FEATURE:
<221> NAME/KEY: variant
<222> LOCATION: (18)..(18)
<223> OTHER INFORMATION: may be replaced by N
<220> FEATURE:
<221> NAME/KEY: variant
<222> LOCATION: (19)..(19)
<223> OTHER INFORMATION: may be replaced by M
<220> FEATURE:
<221> NAME/KEY: variant
<222> LOCATION: (23)..(23)
<223> OTHER INFORMATION: may be replaced by N
<220> FEATURE:
<221> NAME/KEY: variant
<222> LOCATION: (24)..(24)
<223> OTHER INFORMATION: may be replaced by A
<220> FEATURE:
<221> NAME/KEY: variant
<222> LOCATION: (25)..(25)
<223> OTHER INFORMATION: may be replaced by E
<220> FEATURE:
<221> NAME/KEY: variant
<222> LOCATION: (29)..(29)
<223> OTHER INFORMATION: may be replaced by G
<220> FEATURE:
<221> NAME/KEY: variant
```

```
<222> LOCATION: (35)..(35)
<223> OTHER INFORMATION: may be replaced by K or I
<220> FEATURE:
<221> NAME/KEY: variant
<222> LOCATION: (40)..(40)
<223> OTHER INFORMATION: may be replaced by Q or T
<220> FEATURE:
<221> NAME/KEY: variant
<222> LOCATION: (42)..(42)
<223> OTHER INFORMATION: may be replaced by A, K, or T
<220> FEATURE:
<221> NAME/KEY: variant
<222> LOCATION: (43)..(43)
<223> OTHER INFORMATION: may be replaced by S, N, or C
<220> FEATURE:
<221> NAME/KEY: variant
<222> LOCATION: (44)..(44)
<223> OTHER INFORMATION: may be replaced by L or V
<220> FEATURE:
<221> NAME/KEY: variant
<222> LOCATION: (46)..(46)
<223> OTHER INFORMATION: may be replaced by C or A
<220> FEATURE:
<221> NAME/KEY: variant
<222> LOCATION: (47)..(47)
<223> OTHER INFORMATION: may be replaced by C
<220> FEATURE:
<221> NAME/KEY: variant
<222> LOCATION: (49)..(49)
<223> OTHER INFORMATION: may be replaced by Q
<220> FEATURE:
<221> NAME/KEY: variant
<222> LOCATION: (50)..(50)
<223> OTHER INFORMATION: may be replaced by C
<220> FEATURE:
<221> NAME/KEY: variant
<222> LOCATION: (51)..(51)
<223> OTHER INFORMATION: may be replaced by C
<220> FEATURE:
<221> NAME/KEY: variant
<222> LOCATION: (53)..(53)
<223> OTHER INFORMATION: may be replaced by E or C
<220> FEATURE:
<221> NAME/KEY: variant
<222> LOCATION: (54)..(54)
<223> OTHER INFORMATION: may be replaced by S, or deleted
<220> FEATURE:
<221> NAME/KEY: variant
<222> LOCATION: (57)..(57)
<223> OTHER INFORMATION: may be deleted
<220> FEATURE:
<221> NAME/KEY: variant
<222> LOCATION: (58)..(58)
<223> OTHER INFORMATION: may be replaced by K, or deleted

<400> SEQUENCE: 1

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Gly Glu Ala
        35                  40                  45

Lys Lys Leu Asn Asp Ala Gln Ala Pro Pro
    50                  55

<210> SEQ ID NO 2
<211> LENGTH: 58
<212> TYPE: PRT
<213> ORGANISM: Artificial Sequence
<220> FEATURE:
<223> OTHER INFORMATION: consensus sequence 2
<220> FEATURE:
<221> NAME/KEY: variant
<222> LOCATION: (1)..(1)
```

```
<223> OTHER INFORMATION: may be deleted
<220> FEATURE:
<221> NAME/KEY: variant
<222> LOCATION: (2)..(2)
<223> OTHER INFORMATION: may be replaced by D, or deleted
<220> FEATURE:
<221> NAME/KEY: variant
<222> LOCATION: (3)..(3)
<223> OTHER INFORMATION: may be replaced by N or deleted
<220> FEATURE:
<221> NAME/KEY: variant
<222> LOCATION: (4)..(4)
<223> OTHER INFORMATION: may be replaced by Q, or deleted
<220> FEATURE:
<221> NAME/KEY: variant
<222> LOCATION: (5)..(5)
<223> OTHER INFORMATION: may be replaced by F, or deleted
<220> FEATURE:
<221> NAME/KEY: variant
<222> LOCATION: (6)..(6)
<223> OTHER INFORMATION: may be deleted
<220> FEATURE:
<221> NAME/KEY: variant
<222> LOCATION: (7)..(7)
<223> OTHER INFORMATION: may be replaced by E
<220> FEATURE:
<221> NAME/KEY: variant
<222> LOCATION: (8)..(8)
<223> OTHER INFORMATION: may be replaced by A or E
<220> FEATURE:
<221> NAME/KEY: variant
<222> LOCATION: (11)..(11)
<223> OTHER INFORMATION: may be replaced by S, I, or E
<220> FEATURE:
<221> NAME/KEY: variant
<222> LOCATION: (25)..(25)
<223> OTHER INFORMATION: may be replaced by E
<220> FEATURE:
<221> NAME/KEY: variant
<222> LOCATION: (35)..(35)
<223> OTHER INFORMATION: may be replaced by I
<220> FEATURE:
<221> NAME/KEY: variant
<222> LOCATION: (40)..(40)
<223> OTHER INFORMATION: may be replaced by Q or T
<220> FEATURE:
<221> NAME/KEY: variant
<222> LOCATION: (43)..(43)
<223> OTHER INFORMATION: may be replaced by S, or C
<220> FEATURE:
<221> NAME/KEY: variant
<222> LOCATION: (44)..(44)
<223> OTHER INFORMATION: may be replaced by L or V
<220> FEATURE:
<221> NAME/KEY: variant
<222> LOCATION: (46)..(46)
<223> OTHER INFORMATION: may be replaced by C or A
<220> FEATURE:
<221> NAME/KEY: variant
<222> LOCATION: (47)..(47)
<223> OTHER INFORMATION: may be replaced by C
<220> FEATURE:
<221> NAME/KEY: variant
<222> LOCATION: (49)..(49)
<223> OTHER INFORMATION: may be replaced by Q
<220> FEATURE:
<221> NAME/KEY: variant
<222> LOCATION: (50)..(50)
<223> OTHER INFORMATION: may be replaced by C
<220> FEATURE:
<221> NAME/KEY: variant
<222> LOCATION: (51)..(51)
<223> OTHER INFORMATION: may be replaced by  C
<220> FEATURE:
<221> NAME/KEY: variant
<222> LOCATION: (53)..(53)
<223> OTHER INFORMATION: may be replaced by E or C
<220> FEATURE:
<221> NAME/KEY: variant
```

```
<222> LOCATION: (54)..(54)
<223> OTHER INFORMATION: may be replaced by S
<220> FEATURE:
<221> NAME/KEY: variant
<222> LOCATION: (57)..(57)
<223> OTHER INFORMATION: may be deleted
<220> FEATURE:
<221> NAME/KEY: variant
<222> LOCATION: (58)..(58)
<223> OTHER INFORMATION: may be replaced by K, or deleted

<400> SEQUENCE: 2

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Gly Glu Ala
        35                  40                  45

Lys Lys Leu Asn Asp Ala Gln Ala Pro Pro
    50                  55

<210> SEQ ID NO 3
<211> LENGTH: 58
<212> TYPE: PRT
<213> ORGANISM: Artificial Sequence
<220> FEATURE:
<223> OTHER INFORMATION: cs14

<400> SEQUENCE: 3

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Gly Glu Ala
        35                  40                  45

Lys Lys Leu Asn Asp Ala Gln Ala Pro Pro
    50                  55

<210> SEQ ID NO 4
<211> LENGTH: 58
<212> TYPE: PRT
<213> ORGANISM: Artificial Sequence
<220> FEATURE:
<223> OTHER INFORMATION: cs27

<400> SEQUENCE: 4

Ile Ala Ala Lys Phe Asp Glu Ala Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Val Leu Gly Glu Ala
        35                  40                  45

Gln Lys Leu Asn Asp Ser Gln Ala Pro Lys
    50                  55

<210> SEQ ID NO 5
<211> LENGTH: 58
<212> TYPE: PRT
<213> ORGANISM: Artificial Sequence
<220> FEATURE:
<223> OTHER INFORMATION: cs20

<400> SEQUENCE: 5
```

```
Ile Asp Ser Lys Phe Asp Glu Ala Gln Gln Ala Ala Phe Tyr Glu Ile
1               5                   10                  15

Leu His Leu Pro Ser Leu Thr Glu Asp Gln Arg Asn Ala Phe Ile Gln
            20                  25                  30

Ser Leu Arg Asp Asp Pro Ser Thr Ser Leu Ser Leu Leu Gly Glu Ala
        35                  40                  45

Lys Lys Leu Asn Asp Ala Gln Ala Pro Pro
    50                  55
```

<210> SEQ ID NO 6
<211> LENGTH: 58
<212> TYPE: PRT
<213> ORGANISM: Artificial Sequence
<220> FEATURE:
<223> OTHER INFORMATION: cs42

<400> SEQUENCE: 6

```
Ile Asp Ala Lys His Asp Glu Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Gln Ser Leu Glu Ile Leu Gly Glu Ala
        35                  40                  45

Lys Lys Leu Asn Glu Ser Gln Ala Pro Lys
    50                  55
```

<210> SEQ ID NO 7
<211> LENGTH: 58
<212> TYPE: PRT
<213> ORGANISM: Artificial Sequence
<220> FEATURE:
<223> OTHER INFORMATION: cs26

<400> SEQUENCE: 7

```
Ile Ala Ala Gln His Asp Lys Asp Gln Gln Ala Ala Phe Tyr Glu Ile
1               5                   10                  15

Leu His Leu Pro Asn Leu Thr Glu Gln Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55
```

<210> SEQ ID NO 8
<211> LENGTH: 58
<212> TYPE: PRT
<213> ORGANISM: Artificial Sequence
<220> FEATURE:
<223> OTHER INFORMATION: cs24

<400> SEQUENCE: 8

```
Ile Ala Ala Gln His Asp Lys Glu Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Gly Glu Ala
        35                  40                  45

Lys Lys Leu Asn Asp Ala Gln Ala Pro Lys
    50                  55
```

<210> SEQ ID NO 9
<211> LENGTH: 58
<212> TYPE: PRT
<213> ORGANISM: Artificial Sequence
<220> FEATURE:
<223> OTHER INFORMATION: cs17

<400> SEQUENCE: 9

Ile Asp Ser Lys Phe Asp Glu Ala Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Ser Leu Leu Gly Glu Ala
        35                  40                  45

Lys Lys Leu Asn Asp Ala Gln Ala Pro Pro
    50                  55

<210> SEQ ID NO 10
<211> LENGTH: 58
<212> TYPE: PRT
<213> ORGANISM: Artificial Sequence
<220> FEATURE:
<223> OTHER INFORMATION: cs25

<400> SEQUENCE: 10

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 11
<211> LENGTH: 58
<212> TYPE: PRT
<213> ORGANISM: Artificial Sequence
<220> FEATURE:
<223> OTHER INFORMATION: cs47h3

<400> SEQUENCE: 11

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Val Leu Gly Glu Ala
        35                  40                  45

Gln Lys Leu Asn Asp Ser Gln Ala Pro Lys
    50                  55

<210> SEQ ID NO 12
<211> LENGTH: 58
<212> TYPE: PRT
<213> ORGANISM: Artificial Sequence
<220> FEATURE:
<223> OTHER INFORMATION: cs47h4

<400> SEQUENCE: 12

Ile Ala Ala Lys His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln

```
                        20                  25                  30

Ser Leu Arg Asp Asp Pro Ser Val Ser Leu Glu Val Leu Gly Glu Ala
        35                  40                  45

Gln Lys Leu Asn Asp Ser Gln Ala Pro Lys
    50                  55

<210> SEQ ID NO 13
<211> LENGTH: 58
<212> TYPE: PRT
<213> ORGANISM: Artificial Sequence
<220> FEATURE:
<223> OTHER INFORMATION: cs74h1

<400> SEQUENCE: 13

Ile Ala Ala Lys Phe Asp Glu Ala Gln Gln Ala Ala Phe Tyr Glu Ile
1               5                   10                  15

Leu His Leu Pro Asn Leu Thr Glu Asp Gln Arg Asn Ala Phe Ile Gln
                20                  25                  30

Ser Leu Arg Asp Asp Pro Ser Val Ser Leu Glu Ile Leu Gly Glu Ala
        35                  40                  45

Lys Lys Leu Asn Asp Ala Gln Ala Pro Pro
    50                  55

<210> SEQ ID NO 14
<211> LENGTH: 58
<212> TYPE: PRT
<213> ORGANISM: Artificial Sequence
<220> FEATURE:
<223> OTHER INFORMATION: cs74h2

<400> SEQUENCE: 14

Ile Ala Ala Lys Phe Asp Glu Ala Gln Gln Ala Ala Phe Tyr Glu Ile
1               5                   10                  15

Leu His Leu Pro Asn Leu Thr Glu Gly Gln Arg Asn Ala Phe Ile Gln
                20                  25                  30

Ser Leu Arg Asp Asp Pro Ser Val Ser Leu Glu Ile Leu Gly Glu Ala
        35                  40                  45

Lys Lys Leu Asn Asp Ala Gln Ala Pro Pro
    50                  55

<210> SEQ ID NO 15
<211> LENGTH: 58
<212> TYPE: PRT
<213> ORGANISM: Artificial Sequence
<220> FEATURE:
<223> OTHER INFORMATION: cs41

<400> SEQUENCE: 15

Ile Ala Ala Lys His Asp Glu Asp Gln Gln Ala Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Arg Asp Asp Pro Ser Val Ser Leu Glu Ile Leu Gly Glu Ala
        35                  40                  45

Lys Lys Leu Asn Asp Ser Gln Ala Pro Lys
    50                  55

<210> SEQ ID NO 16
<211> LENGTH: 58
<212> TYPE: PRT
<213> ORGANISM: Artificial Sequence
```

```
<220> FEATURE:
<223> OTHER INFORMATION: cs43

<400> SEQUENCE: 16

Ile Ala Ala Lys His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Arg Asp Asp Pro Ser Val Ser Leu Glu Ile Leu Gly Glu Ala
            35                  40                  45

Lys Lys Leu Asn Asp Ser Gln Ala Pro Lys
    50                  55

<210> SEQ ID NO 17
<211> LENGTH: 58
<212> TYPE: PRT
<213> ORGANISM: Artificial Sequence
<220> FEATURE:
<223> OTHER INFORMATION: cs14 43C

<400> SEQUENCE: 17

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Asn Ala Phe Ile Gln
                20                  25                  30

Ser Leu Arg Asp Asp Pro Ser Val Ser Leu Cys Ile Leu Gly Glu Ala
            35                  40                  45

Lys Lys Leu Asn Asp Ala Gln Ala Pro Pro
    50                  55

<210> SEQ ID NO 18
<211> LENGTH: 58
<212> TYPE: PRT
<213> ORGANISM: Artificial Sequence
<220> FEATURE:
<223> OTHER INFORMATION: cs14 46C

<400> SEQUENCE: 18

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Asn Ala Phe Ile Gln
                20                  25                  30

Ser Leu Arg Asp Asp Pro Ser Val Ser Leu Glu Ile Leu Cys Glu Ala
            35                  40                  45

Lys Lys Leu Asn Asp Ala Gln Ala Pro Pro
    50                  55

<210> SEQ ID NO 19
<211> LENGTH: 58
<212> TYPE: PRT
<213> ORGANISM: Artificial Sequence
<220> FEATURE:
<223> OTHER INFORMATION: cs14 47C

<400> SEQUENCE: 19

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Asn Ala Phe Ile Gln
                20                  25                  30

Ser Leu Arg Asp Asp Pro Ser Val Ser Leu Glu Ile Leu Gly Cys Ala
            35                  40                  45
```

```
Lys Lys Leu Asn Asp Ala Gln Ala Pro Pro
    50                  55

<210> SEQ ID NO 20
<211> LENGTH: 58
<212> TYPE: PRT
<213> ORGANISM: Artificial Sequence
<220> FEATURE:
<223> OTHER INFORMATION: cs14 11S 46C

<400> SEQUENCE: 20

Ile Ala Ala Lys His Asp Lys Asp Gln Gln Ser Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Cys Glu Ala
        35                  40                  45

Lys Lys Leu Asn Asp Ala Gln Ala Pro Pro
    50                  55

<210> SEQ ID NO 21
<211> LENGTH: 58
<212> TYPE: PRT
<213> ORGANISM: Artificial Sequence
<220> FEATURE:
<223> OTHER INFORMATION: cs27 43C

<400> SEQUENCE: 21

Ile Ala Ala Lys Phe Asp Glu Ala Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Cys Val Leu Gly Glu Ala
        35                  40                  45

Gln Lys Leu Asn Asp Ser Gln Ala Pro Lys
    50                  55

<210> SEQ ID NO 22
<211> LENGTH: 58
<212> TYPE: PRT
<213> ORGANISM: Artificial Sequence
<220> FEATURE:
<223> OTHER INFORMATION: cs27 46C

<400> SEQUENCE: 22

Ile Ala Ala Lys Phe Asp Glu Ala Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Val Leu Cys Glu Ala
        35                  40                  45

Gln Lys Leu Asn Asp Ser Gln Ala Pro Lys
    50                  55

<210> SEQ ID NO 23
<211> LENGTH: 58
<212> TYPE: PRT
<213> ORGANISM: Artificial Sequence
<220> FEATURE:
<223> OTHER INFORMATION: cs27 47C

<400> SEQUENCE: 23
```

```
Ile Ala Ala Lys Phe Asp Glu Ala Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Val Leu Gly Cys Ala
        35                  40                  45

Gln Lys Leu Asn Asp Ser Gln Ala Pro Lys
    50                  55
```

<210> SEQ ID NO 24
<211> LENGTH: 58
<212> TYPE: PRT
<213> ORGANISM: Artificial Sequence
<220> FEATURE:
<223> OTHER INFORMATION: cs27 11S 46C

<400> SEQUENCE: 24

```
Ile Ala Ala Lys Phe Asp Glu Ala Gln Gln Ser Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Val Leu Cys Glu Ala
        35                  40                  45

Gln Lys Leu Asn Asp Ser Gln Ala Pro Lys
    50                  55
```

<210> SEQ ID NO 25
<211> LENGTH: 116
<212> TYPE: PRT
<213> ORGANISM: Artificial Sequence
<220> FEATURE:
<223> OTHER INFORMATION: cs27 46C dimer

<400> SEQUENCE: 25

```
Ile Ala Ala Lys Phe Asp Glu Ala Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Val Leu Cys Glu Ala
        35                  40                  45

Gln Lys Leu Asn Asp Ser Gln Ala Pro Lys Ile Ala Ala Lys Phe Asp
    50                  55                  60

Glu Ala Gln Gln Ala Ala Phe Tyr Glu Ile Leu His Leu Pro Asn Leu
65                  70                  75                  80

Thr Glu Glu Gln Arg Asn Ala Phe Ile Gln Ser Leu Arg Asp Asp Pro
                85                  90                  95

Ser Val Ser Leu Glu Val Leu Cys Glu Ala Gln Lys Leu Asn Asp Ser
            100                 105                 110

Gln Ala Pro Lys
        115
```

<210> SEQ ID NO 26
<211> LENGTH: 58
<212> TYPE: PRT
<213> ORGANISM: Artificial Sequence
<220> FEATURE:
<223> OTHER INFORMATION: cs26 43C

<400> SEQUENCE: 26

```
Ile Ala Ala Gln His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Cys Ile Leu Ala Glu Ala
        35                  40                  45

Lys Lys Leu Asn Asp Ala Gln Ala Pro Lys
    50                  55
```

<210> SEQ ID NO 27
<211> LENGTH: 58
<212> TYPE: PRT
<213> ORGANISM: Artificial Sequence
<220> FEATURE:
<223> OTHER INFORMATION: cs26 46C

<400> SEQUENCE: 27

```
Ile Ala Ala Gln His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Cys Glu Ala
        35                  40                  45

Lys Lys Leu Asn Asp Ala Gln Ala Pro Lys
    50                  55
```

<210> SEQ ID NO 28
<211> LENGTH: 58
<212> TYPE: PRT
<213> ORGANISM: Artificial Sequence
<220> FEATURE:
<223> OTHER INFORMATION: cs26 47C

<400> SEQUENCE: 28

```
Ile Ala Ala Gln His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Cys Ala
        35                  40                  45

Lys Lys Leu Asn Asp Ala Gln Ala Pro Lys
    50                  55
```

<210> SEQ ID NO 29
<211> LENGTH: 58
<212> TYPE: PRT
<213> ORGANISM: Artificial Sequence
<220> FEATURE:
<223> OTHER INFORMATION: cs26 11S 46C

<400> SEQUENCE: 29

```
Ile Ala Ala Gln His Asp Lys Asp Gln Gln Ser Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Cys Glu Ala
        35                  40                  45

Lys Lys Leu Asn Asp Ala Gln Ala Pro Lys
    50                  55
```

```
<210> SEQ ID NO 30
<211> LENGTH: 58
<212> TYPE: PRT
<213> ORGANISM: Artificial Sequence
<220> FEATURE:
<223> OTHER INFORMATION: cs26 9H 46C

<400> SEQUENCE: 30

Ile Ala Ala Gln His Asp Lys Asp His Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Cys Glu Ala
        35                  40                  45

Lys Lys Leu Asn Asp Ala Gln Ala Pro Lys
    50                  55

<210> SEQ ID NO 31
<211> LENGTH: 58
<212> TYPE: PRT
<213> ORGANISM: Artificial Sequence
<220> FEATURE:
<223> OTHER INFORMATION: cs26 36H 46C

<400> SEQUENCE: 31

Ile Ala Ala Gln His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg His Asp Pro Ser Val Ser Leu Glu Ile Leu Cys Glu Ala
        35                  40                  45

Lys Lys Leu Asn Asp Ala Gln Ala Pro Lys
    50                  55

<210> SEQ ID NO 32
<211> LENGTH: 116
<212> TYPE: PRT
<213> ORGANISM: Artificial Sequence
<220> FEATURE:
<223> OTHER INFORMATION: cs26 46C dimer

<400> SEQUENCE: 32

Ile Ala Ala Gln His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Cys Glu Ala
        35                  40                  45

Lys Lys Leu Asn Asp Ala Gln Ala Pro Lys Ile Ala Ala Gln His Asp
    50                  55                  60

Lys Asp Gln Gln Ala Ala Phe Tyr Glu Ile Leu His Leu Pro Asn Leu
65                  70                  75                  80

Thr Glu Glu Gln Arg Asn Ala Phe Ile Gln Ser Leu Arg Asp Asp Pro
                85                  90                  95

Ser Val Ser Leu Glu Ile Leu Cys Glu Ala Lys Lys Leu Asn Asp Ala
            100                 105                 110

Gln Ala Pro Lys
    115

<210> SEQ ID NO 33
```

```
<211> LENGTH: 55
<212> TYPE: PRT
<213> ORGANISM: Artificial Sequence
<220> FEATURE:
<223> OTHER INFORMATION: cs26 delN 46C

<400> SEQUENCE: 33

Ala His Asp Lys Asp Gln Gln Ala Ala Phe Tyr Glu Ile Leu His Leu
1               5                   10                  15

Pro Asn Leu Thr Glu Glu Gln Arg Asn Ala Phe Ile Gln Ser Leu Arg
            20                  25                  30

Asp Asp Pro Ser Val Ser Leu Glu Ile Leu Cys Glu Ala Lys Lys Leu
        35                  40                  45

Asn Asp Ala Gln Ala Pro Lys
    50                  55

<210> SEQ ID NO 34
<211> LENGTH: 53
<212> TYPE: PRT
<213> ORGANISM: Artificial Sequence
<220> FEATURE:
<223> OTHER INFORMATION: cs26 delNC 46C

<400> SEQUENCE: 34

Gln His Asp Lys Asp Gln Gln Ala Ala Phe Tyr Glu Ile Leu His Leu
1               5                   10                  15

Pro Asn Leu Thr Glu Glu Gln Arg Asn Ala Phe Ile Gln Ser Leu Arg
            20                  25                  30

Asp Asp Pro Ser Val Ser Leu Glu Ile Leu Cys Glu Ala Lys Lys Leu
        35                  40                  45

Asn Asp Ala Gln Ala
    50

<210> SEQ ID NO 35
<211> LENGTH: 174
<212> TYPE: PRT
<213> ORGANISM: Artificial Sequence
<220> FEATURE:
<223> OTHER INFORMATION: cs26 46C trimer

<400> SEQUENCE: 35

Ile Ala Ala Gln His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Cys Glu Ala
        35                  40                  45

Lys Lys Leu Asn Asp Ala Gln Ala Pro Lys Ile Ala Ala Gln His Asp
    50                  55                  60

Lys Asp Gln Gln Ala Ala Phe Tyr Glu Ile Leu His Leu Pro Asn Leu
65                  70                  75                  80

Thr Glu Glu Gln Arg Asn Ala Phe Ile Gln Ser Leu Arg Asp Asp Pro
                85                  90                  95

Ser Val Ser Leu Glu Ile Leu Cys Glu Ala Lys Lys Leu Asn Asp Ala
            100                 105                 110

Gln Ala Pro Lys Ile Ala Ala Gln His Asp Lys Asp Gln Gln Ala Ala
        115                 120                 125

Phe Tyr Glu Ile Leu His Leu Pro Asn Leu Thr Glu Glu Gln Arg Asn
    130                 135                 140
```

```
Ala Phe Ile Gln Ser Leu Arg Asp Asp Pro Ser Val Ser Leu Glu Ile
145                 150                 155                 160

Leu Cys Glu Ala Lys Lys Leu Asn Asp Ala Gln Ala Pro Lys
                165                 170
```

<210> SEQ ID NO 36
<211> LENGTH: 58
<212> TYPE: PRT
<213> ORGANISM: Artificial Sequence
<220> FEATURE:
<223> OTHER INFORMATION: cs24 43C

<400> SEQUENCE: 36

```
Ile Ala Ala Gln His Asp Lys Glu Gln Gln Ala Ala Phe Tyr Glu Ile
1               5                   10                  15

Leu His Leu Pro Asn Leu Thr Glu Asp Gln Arg Asn Ala Phe Ile Gln
                20                  25                  30

Ser Leu Arg Asp Asp Pro Ser Val Ser Leu Cys Ile Leu Gly Glu Ala
            35                  40                  45

Lys Lys Leu Asn Asp Ala Gln Ala Pro Lys
        50                  55
```

<210> SEQ ID NO 37
<211> LENGTH: 58
<212> TYPE: PRT
<213> ORGANISM: Artificial Sequence
<220> FEATURE:
<223> OTHER INFORMATION: cs24 46C

<400> SEQUENCE: 37

```
Ile Ala Ala Gln His Asp Lys Glu Gln Gln Ala Ala Phe Tyr Glu Ile
1               5                   10                  15

Leu His Leu Pro Asn Leu Thr Glu Asp Gln Arg Asn Ala Phe Ile Gln
                20                  25                  30

Ser Leu Arg Asp Asp Pro Ser Val Ser Leu Glu Ile Leu Cys Glu Ala
            35                  40                  45

Lys Lys Leu Asn Asp Ala Gln Ala Pro Lys
        50                  55
```

<210> SEQ ID NO 38
<211> LENGTH: 58
<212> TYPE: PRT
<213> ORGANISM: Artificial Sequence
<220> FEATURE:
<223> OTHER INFORMATION: cs24 47C

<400> SEQUENCE: 38

```
Ile Ala Ala Gln His Asp Lys Glu Gln Gln Ala Ala Phe Tyr Glu Ile
1               5                   10                  15

Leu His Leu Pro Asn Leu Thr Glu Asp Gln Arg Asn Ala Phe Ile Gln
                20                  25                  30

Ser Leu Arg Asp Asp Pro Ser Val Ser Leu Glu Ile Leu Gly Cys Ala
            35                  40                  45

Lys Lys Leu Asn Asp Ala Gln Ala Pro Lys
        50                  55
```

<210> SEQ ID NO 39
<211> LENGTH: 58
<212> TYPE: PRT
<213> ORGANISM: Artificial Sequence
<220> FEATURE:
<223> OTHER INFORMATION: cs24 11S 46C

<400> SEQUENCE: 39

Ile Ala Ala Gln His Asp Lys Glu Gln Gln Ser Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Cys Glu Ala
        35                  40                  45

Lys Lys Leu Asn Asp Ala Gln Ala Pro Lys
    50                  55

<210> SEQ ID NO 40
<211> LENGTH: 58
<212> TYPE: PRT
<213> ORGANISM: Artificial Sequence
<220> FEATURE:
<223> OTHER INFORMATION: cs47h3 43C

<400> SEQUENCE: 40

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Cys Val Leu Gly Glu Ala
        35                  40                  45

Gln Lys Leu Asn Asp Ser Gln Ala Pro Lys
    50                  55

<210> SEQ ID NO 41
<211> LENGTH: 58
<212> TYPE: PRT
<213> ORGANISM: Artificial Sequence
<220> FEATURE:
<223> OTHER INFORMATION: cs47h3 46C

<400> SEQUENCE: 41

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Val Leu Cys Glu Ala
        35                  40                  45

Gln Lys Leu Asn Asp Ser Gln Ala Pro Lys
    50                  55

<210> SEQ ID NO 42
<211> LENGTH: 58
<212> TYPE: PRT
<213> ORGANISM: Artificial Sequence
<220> FEATURE:
<223> OTHER INFORMATION: cs47h3 47C

<400> SEQUENCE: 42

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Val Leu Gly Cys Ala
        35                  40                  45

Gln Lys Leu Asn Asp Ser Gln Ala Pro Lys

<210> SEQ ID NO 43
<211> LENGTH: 58
<212> TYPE: PRT
<213> ORGANISM: Artificial Sequence
<220> FEATURE:
<223> OTHER INFORMATION: cs47h3 11S 46C

<400> SEQUENCE: 43

Ile Ala Ala Lys His Asp Lys Asp Gln Gln Ser Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Val Leu Cys Glu Ala
        35                  40                  45

Gln Lys Leu Asn Asp Ser Gln Ala Pro Lys
    50                  55

<210> SEQ ID NO 44
<211> LENGTH: 58
<212> TYPE: PRT
<213> ORGANISM: Artificial Sequence
<220> FEATURE:
<223> OTHER INFORMATION: cs47h4 43C

<400> SEQUENCE: 44

Ile Ala Ala Lys His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Cys Val Leu Gly Glu Ala
        35                  40                  45

Gln Lys Leu Asn Asp Ser Gln Ala Pro Lys
    50                  55

<210> SEQ ID NO 45
<211> LENGTH: 58
<212> TYPE: PRT
<213> ORGANISM: Artificial Sequence
<220> FEATURE:
<223> OTHER INFORMATION: cs47h4 46C

<400> SEQUENCE: 45

Ile Ala Ala Lys His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Val Leu Cys Glu Ala
        35                  40                  45

Gln Lys Leu Asn Asp Ser Gln Ala Pro Lys
    50                  55

<210> SEQ ID NO 46
<211> LENGTH: 58
<212> TYPE: PRT
<213> ORGANISM: Artificial Sequence
<220> FEATURE:
<223> OTHER INFORMATION: cs47h4 47C

<400> SEQUENCE: 46

Ile Ala Ala Lys His Asp Lys Asp Gln Gln Ala Ala Phe Tyr Glu Ile

```
1               5                   10                  15
Leu His Leu Pro Asn Leu Thr Glu Glu Gln Arg Asn Ala Phe Ile Gln
            20                  25                  30

Ser Leu Arg Asp Asp Pro Ser Val Ser Leu Glu Val Leu Gly Cys Ala
        35                  40                  45

Gln Lys Leu Asn Asp Ser Gln Ala Pro Lys
    50                  55
```

<210> SEQ ID NO 47
<211> LENGTH: 58
<212> TYPE: PRT
<213> ORGANISM: Artificial Sequence
<220> FEATURE:
<223> OTHER INFORMATION: cs74h1 43C

<400> SEQUENCE: 47

```
Ile Ala Ala Lys Phe Asp Glu Ala Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Cys Ile Leu Gly Glu Ala
        35                  40                  45

Lys Lys Leu Asn Asp Ala Gln Ala Pro Pro
    50                  55
```

<210> SEQ ID NO 48
<211> LENGTH: 58
<212> TYPE: PRT
<213> ORGANISM: Artificial Sequence
<220> FEATURE:
<223> OTHER INFORMATION: cs74h1 46C

<400> SEQUENCE: 48

```
Ile Ala Ala Lys Phe Asp Glu Ala Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Cys Glu Ala
        35                  40                  45

Lys Lys Leu Asn Asp Ala Gln Ala Pro Pro
    50                  55
```

<210> SEQ ID NO 49
<211> LENGTH: 58
<212> TYPE: PRT
<213> ORGANISM: Artificial Sequence
<220> FEATURE:
<223> OTHER INFORMATION: cs74h1 47C

<400> SEQUENCE: 49

```
Ile Ala Ala Lys Phe Asp Glu Ala Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Gly Cys Ala
        35                  40                  45

Lys Lys Leu Asn Asp Ala Gln Ala Pro Pro
    50                  55
```

<210> SEQ ID NO 50

```
<211> LENGTH: 58
<212> TYPE: PRT
<213> ORGANISM: Artificial Sequence
<220> FEATURE:
<223> OTHER INFORMATION: cs74h2 43C

<400> SEQUENCE: 50

Ile Ala Ala Lys Phe Asp Glu Ala Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Cys Ile Leu Gly Glu Ala
        35                  40                  45

Lys Lys Leu Asn Asp Ala Gln Ala Pro Pro
    50                  55

<210> SEQ ID NO 51
<211> LENGTH: 58
<212> TYPE: PRT
<213> ORGANISM: Artificial Sequence
<220> FEATURE:
<223> OTHER INFORMATION: cs74h2 46C

<400> SEQUENCE: 51

Ile Ala Ala Lys Phe Asp Glu Ala Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Cys Glu Ala
        35                  40                  45

Lys Lys Leu Asn Asp Ala Gln Ala Pro Pro
    50                  55

<210> SEQ ID NO 52
<211> LENGTH: 58
<212> TYPE: PRT
<213> ORGANISM: Artificial Sequence
<220> FEATURE:
<223> OTHER INFORMATION: cs74h2 47C

<400> SEQUENCE: 52

Ile Ala Ala Lys Phe Asp Glu Ala Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Gly Cys Ala
        35                  40                  45

Lys Lys Leu Asn Asp Ala Gln Ala Pro Pro
    50                  55

<210> SEQ ID NO 53
<211> LENGTH: 58
<212> TYPE: PRT
<213> ORGANISM: Artificial Sequence
<220> FEATURE:
<223> OTHER INFORMATION: cs20 46C

<400> SEQUENCE: 53

Ile Asp Ser Lys Phe Asp Glu Ala Gln Gln Ala Ala Phe Tyr Glu Ile
1               5                   10                  15

Leu His Leu Pro Ser Leu Thr Glu Asp Gln Arg Asn Ala Phe Ile Gln
            20                  25                  30
```

-continued

Ser Leu Arg Asp Asp Pro Ser Thr Ser Leu Ser Leu Leu Cys Glu Ala
        35                  40                  45

Lys Lys Leu Asn Asp Ala Gln Ala Pro Pro
    50                  55

<210> SEQ ID NO 54
<211> LENGTH: 58
<212> TYPE: PRT
<213> ORGANISM: Artificial Sequence
<220> FEATURE:
<223> OTHER INFORMATION: cs20 43C

<400> SEQUENCE: 54

Ile Asp Ser Lys Phe Asp Glu Ala Gln Gln Ala Ala Phe Tyr Glu Ile
1               5                   10                  15

Leu His Leu Pro Ser Leu Thr Glu Asp Gln Arg Asn Ala Phe Ile Gln
            20                  25                  30

Ser Leu Arg Asp Asp Pro Ser Thr Ser Leu Cys Leu Leu Gly Glu Ala
        35                  40                  45

Lys Lys Leu Asn Asp Ala Gln Ala Pro Pro
    50                  55

<210> SEQ ID NO 55
<211> LENGTH: 58
<212> TYPE: PRT
<213> ORGANISM: Artificial Sequence
<220> FEATURE:
<223> OTHER INFORMATION: cs20 47C

<400> SEQUENCE: 55

Ile Asp Ser Lys Phe Asp Glu Ala Gln Gln Ala Ala Phe Tyr Glu Ile
1               5                   10                  15

Leu His Leu Pro Ser Leu Thr Glu Asp Gln Arg Asn Ala Phe Ile Gln
            20                  25                  30

Ser Leu Arg Asp Asp Pro Ser Thr Ser Leu Ser Leu Leu Gly Cys Ala
        35                  40                  45

Lys Lys Leu Asn Asp Ala Gln Ala Pro Pro
    50                  55

<210> SEQ ID NO 56
<211> LENGTH: 58
<212> TYPE: PRT
<213> ORGANISM: Artificial Sequence
<220> FEATURE:
<223> OTHER INFORMATION: cs20 11S 46C

<400> SEQUENCE: 56

Ile Asp Ser Lys Phe Asp Glu Ala Gln Gln Ser Ala Phe Tyr Glu Ile
1               5                   10                  15

Leu His Leu Pro Ser Leu Thr Glu Asp Gln Arg Asn Ala Phe Ile Gln
            20                  25                  30

Ser Leu Arg Asp Asp Pro Ser Thr Ser Leu Ser Leu Leu Cys Glu Ala
        35                  40                  45

Lys Lys Leu Asn Asp Ala Gln Ala Pro Pro
    50                  55

<210> SEQ ID NO 57
<211> LENGTH: 58
<212> TYPE: PRT
<213> ORGANISM: Artificial Sequence
<220> FEATURE:

<223> OTHER INFORMATION: cs17 46C

<400> SEQUENCE: 57

Ile Asp Ser Lys Phe Asp Glu Ala Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Ser Leu Cys Glu Ala
        35                  40                  45

Lys Lys Leu Asn Asp Ala Gln Ala Pro Pro
    50                  55

<210> SEQ ID NO 58
<211> LENGTH: 58
<212> TYPE: PRT
<213> ORGANISM: Artificial Sequence
<220> FEATURE:
<223> OTHER INFORMATION: cs42 46C

<400> SEQUENCE: 58

Ile Asp Ala Lys His Asp Glu Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Gln Ser Leu Glu Ile Leu Cys Glu Ala
        35                  40                  45

Lys Lys Leu Asn Glu Ser Gln Ala Pro Lys
    50                  55

<210> SEQ ID NO 59
<211> LENGTH: 58
<212> TYPE: PRT
<213> ORGANISM: Artificial Sequence
<220> FEATURE:
<223> OTHER INFORMATION: cs42 47C

<400> SEQUENCE: 59

Ile Asp Ala Lys His Asp Glu Asp Gln Gln Ala Ala Phe Tyr Glu Ile
1               5                   10                  15

Leu His Leu Pro Asn Leu Thr Glu Gln Arg Asn Ala Phe Ile Gln
            20                  25                  30

Ser Leu Arg Asp Asp Pro Ser Gln Ser Leu Glu Ile Leu Gly Cys Ala
        35                  40                  45

Lys Lys Leu Asn Glu Ser Gln Ala Pro Lys
    50                  55

<210> SEQ ID NO 60
<211> LENGTH: 58
<212> TYPE: PRT
<213> ORGANISM: Artificial Sequence
<220> FEATURE:
<223> OTHER INFORMATION: cs42 43C

<400> SEQUENCE: 60

Ile Asp Ala Lys His Asp Glu Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Gln Ser Leu Cys Ile Leu Gly Glu Ala
        35                  40                  45

```
Lys Lys Leu Asn Glu Ser Gln Ala Pro Lys
    50                  55

<210> SEQ ID NO 61
<211> LENGTH: 58
<212> TYPE: PRT
<213> ORGANISM: Artificial Sequence
<220> FEATURE:
<223> OTHER INFORMATION: cs42 11S 46C

<400> SEQUENCE: 61

Ile Asp Ala Lys His Asp Glu Asp Gln Gln Ser Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Gln Ser Leu Glu Ile Leu Cys Glu Ala
        35                  40                  45

Lys Lys Leu Asn Glu Ser Gln Ala Pro Lys
    50                  55

<210> SEQ ID NO 62
<211> LENGTH: 58
<212> TYPE: PRT
<213> ORGANISM: Artificial Sequence
<220> FEATURE:
<223> OTHER INFORMATION: cs41 46C

<400> SEQUENCE: 62

Ile Ala Ala Lys His Asp Glu Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Cys Glu Ala
        35                  40                  45

Lys Lys Leu Asn Asp Ser Gln Ala Pro Lys
    50                  55

<210> SEQ ID NO 63
<211> LENGTH: 58
<212> TYPE: PRT
<213> ORGANISM: Artificial Sequence
<220> FEATURE:
<223> OTHER INFORMATION: cs28 46C

<400> SEQUENCE: 63

Ile Asp Ala Gln His Asp Glu Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Gln Ser Leu Glu Ile Leu Cys Glu Ala
        35                  40                  45

Lys Lys Leu Asn Glu Ser Gln Ala Pro Lys
    50                  55

<210> SEQ ID NO 64
<211> LENGTH: 58
<212> TYPE: PRT
<213> ORGANISM: Artificial Sequence
<220> FEATURE:
<223> OTHER INFORMATION: cs23 46C

<400> SEQUENCE: 64
```

Ile Ala Ala Lys His Asp Lys Asp Gln Gln Ala Ala Phe Tyr Glu Ile
1               5                   10                  15

Leu His Leu Pro Ser Leu Thr Glu Asp Gln Arg Asn Ala Phe Ile Gln
            20                  25                  30

Ser Leu Arg Asp Asp Pro Ser Thr Ser Leu Ser Ile Leu Cys Glu Ala
        35                  40                  45

Lys Lys Leu Asn Asp Ala Gln Ala Pro Pro
50                  55

<210> SEQ ID NO 65
<211> LENGTH: 58
<212> TYPE: PRT
<213> ORGANISM: Artificial Sequence
<220> FEATURE:
<223> OTHER INFORMATION: cs25 46C

<400> SEQUENCE: 65

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Cys Glu Ala
        35                  40                  45

Lys Lys Leu Asn Asp Ala Gln Ala Pro Lys
50                  55

<210> SEQ ID NO 66
<211> LENGTH: 58
<212> TYPE: PRT
<213> ORGANISM: Artificial Sequence
<220> FEATURE:
<223> OTHER INFORMATION: cs31 46C

<400> SEQUENCE: 66

Ile Ala Ala Lys His Asp Lys Asp Gln Gln Ala Ala Phe Tyr Glu Ile
1               5                   10                  15

Leu His Leu Pro Ser Leu Thr Glu Asp Gln Arg Asn Ala Phe Ile Gln
            20                  25                  30

Ser Leu Arg Asp Asp Pro Ser Val Ser Leu Glu Ile Leu Cys Glu Ala
        35                  40                  45

Lys Lys Leu Asp Asp Ala Gln Ala Pro Lys
50                  55

<210> SEQ ID NO 67
<211> LENGTH: 58
<212> TYPE: PRT
<213> ORGANISM: Artificial Sequence
<220> FEATURE:
<223> OTHER INFORMATION: cs43 46C

<400> SEQUENCE: 67

Ile Ala Ala Lys His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Cys Glu Ala
        35                  40                  45

Lys Lys Leu Asn Asp Ser Gln Ala Pro Lys
50                  55

```
<210> SEQ ID NO 68
<211> LENGTH: 58
<212> TYPE: PRT
<213> ORGANISM: Artificial Sequence
<220> FEATURE:
<223> OTHER INFORMATION: cs44 46C

<400> SEQUENCE: 68

Ile Ala Ala Lys His Asp Lys Asp Gln Gln Ala Ala Phe Tyr Glu Ile
1               5                   10                  15

Leu His Leu Pro Asn Leu Thr Glu Glu Arg Asn Ala Phe Ile Gln
            20                  25                  30

Ser Leu Arg Asp Asp Pro Ser Val Ser Leu Glu Val Leu Cys Glu Ala
        35                  40                  45

Lys Lys Leu Asn Asp Ala Gln Ala Pro Lys
    50                  55

<210> SEQ ID NO 69
<211> LENGTH: 58
<212> TYPE: PRT
<213> ORGANISM: Artificial Sequence
<220> FEATURE:
<223> OTHER INFORMATION: cs45 46C

<400> SEQUENCE: 69

Ile Ala Ala Lys His Asp Lys Asp Gln Gln Ala Ala Phe Tyr Glu Ile
1               5                   10                  15

Leu His Leu Pro Ser Leu Thr Glu Asp Ala Arg Asn Ala Phe Ile Gln
            20                  25                  30

Ser Leu Arg Asp Asp Pro Ser Val Ser Leu Glu Ile Leu Cys Glu Ala
        35                  40                  45

Lys Lys Leu Asp Asp Ala Gln Ala Pro Lys
    50                  55

<210> SEQ ID NO 70
<211> LENGTH: 58
<212> TYPE: PRT
<213> ORGANISM: Artificial Sequence
<220> FEATURE:
<223> OTHER INFORMATION: cs15 46C

<400> SEQUENCE: 70

Ile Asp Asn Lys Phe Asp Glu Ala Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Cys Glu Ala
        35                  40                  45

Lys Lys Leu Asn Asp Ala Gln Ala Pro Pro
    50                  55

<210> SEQ ID NO 71
<211> LENGTH: 58
<212> TYPE: PRT
<213> ORGANISM: Artificial Sequence
<220> FEATURE:
<223> OTHER INFORMATION: cs16 46C

<400> SEQUENCE: 71

Ile Asp Ser Lys Phe Asp Glu Ala Gln Gln Ala Ala Phe Tyr Glu Ile
1               5                   10                  15

Leu His Leu Pro Asn Leu Thr Glu Asp Gln Arg Asn Ala Phe Ile Gln
```

```
                20                  25                  30

Ser Leu Arg Asp Asp Pro Ser Val Ser Leu Glu Ile Leu Cys Glu Ala
         35                  40                  45

Lys Lys Leu Asn Asp Ala Gln Ala Pro Pro
     50                  55

<210> SEQ ID NO 72
<211> LENGTH: 58
<212> TYPE: PRT
<213> ORGANISM: Artificial Sequence
<220> FEATURE:
<223> OTHER INFORMATION: cs35 46C

<400> SEQUENCE: 72

Ile Asp Ala Lys Phe Asp Lys Glu Gln Gln Ala Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Arg Asp Asp Pro Ser Gln Ser Leu Glu Leu Leu Cys Glu Ala
         35                  40                  45

Lys Lys Leu Asn Asp Ala Gln Ala Pro Lys
     50                  55

<210> SEQ ID NO 73
<211> LENGTH: 61
<212> TYPE: PRT
<213> ORGANISM: Artificial Sequence
<220> FEATURE:
<223> OTHER INFORMATION: cs17 11S 46C

<400> SEQUENCE: 73

Ile Asp Ser Ile Asp Ser Lys Phe Asp Glu Ala Gln Gln Ser Ala Phe
1               5                   10                  15

Tyr Glu Ile Leu His Leu Pro Asn Leu Thr Glu Asp Gln Arg Asn Ala
                20                  25                  30

Phe Ile Gln Ser Leu Arg Asp Asp Pro Ser Val Ser Leu Ser Leu Leu
         35                  40                  45

Cys Glu Ala Lys Lys Leu Asn Asp Ala Gln Ala Pro Pro
     50                  55                  60

<210> SEQ ID NO 74
<211> LENGTH: 58
<212> TYPE: PRT
<213> ORGANISM: Artificial Sequence
<220> FEATURE:
<223> OTHER INFORMATION: IB14 43C

<400> SEQUENCE: 74

Pro Ala Ala Lys His Asp Lys Asp Gln Gln Ser Ala Phe Tyr Glu Ile
1               5                   10                  15

Leu His Leu Pro Asn Leu Thr Glu Asp Gln Arg Ser Ala Phe Ile Gln
                20                  25                  30

Ser Leu Lys Asp Asp Pro Ser Val Ser Lys Cys Ile Leu Gly Glu Ala
         35                  40                  45

Lys Lys Leu Asn Asp Ala Gln Ala Pro Pro
     50                  55

<210> SEQ ID NO 75
<211> LENGTH: 58
<212> TYPE: PRT
<213> ORGANISM: Artificial Sequence
```

```
<220> FEATURE:
<223> OTHER INFORMATION: IB14 46C

<400> SEQUENCE: 75

Pro Ala Ala Lys His Asp Lys Asp Gln Gln Ser Ala Phe Tyr Glu Ile
1               5                   10                  15

Leu His Leu Pro Asn Leu Thr Glu Asp Gln Arg Ser Ala Phe Ile Gln
            20                  25                  30

Ser Leu Lys Asp Asp Pro Ser Val Ser Lys Glu Ile Leu Cys Glu Ala
        35                  40                  45

Lys Lys Leu Asn Asp Ala Gln Ala Pro Pro
    50                  55

<210> SEQ ID NO 76
<211> LENGTH: 58
<212> TYPE: PRT
<213> ORGANISM: Artificial Sequence
<220> FEATURE:
<223> OTHER INFORMATION: IB14 47C

<400> SEQUENCE: 76

Pro Ala Ala Lys His Asp Lys Asp Gln Gln Ser Ala Phe Tyr Glu Ile
1               5                   10                  15

Leu His Leu Pro Asn Leu Thr Glu Asp Gln Arg Ser Ala Phe Ile Gln
            20                  25                  30

Ser Leu Lys Asp Asp Pro Ser Val Ser Lys Glu Ile Leu Gly Cys Ala
        35                  40                  45

Lys Lys Leu Asn Asp Ala Gln Ala Pro Pro
    50                  55

<210> SEQ ID NO 77
<211> LENGTH: 58
<212> TYPE: PRT
<213> ORGANISM: Artificial Sequence
<220> FEATURE:
<223> OTHER INFORMATION: IB14 50C

<400> SEQUENCE: 77

Pro Ala Ala Lys His Asp Lys Asp Gln Gln Ser Ala Phe Tyr Glu Ile
1               5                   10                  15

Leu His Leu Pro Asn Leu Thr Glu Asp Gln Arg Ser Ala Phe Ile Gln
            20                  25                  30

Ser Leu Lys Asp Asp Pro Ser Val Ser Lys Glu Ile Leu Gly Glu Ala
        35                  40                  45

Lys Cys Leu Asn Asp Ala Gln Ala Pro Pro
    50                  55

<210> SEQ ID NO 78
<211> LENGTH: 58
<212> TYPE: PRT
<213> ORGANISM: Artificial Sequence
<220> FEATURE:
<223> OTHER INFORMATION: IB14

<400> SEQUENCE: 78

Pro Ala Ala Lys His Asp Lys Asp Gln Gln Ser Ala Phe Tyr Glu Ile
1               5                   10                  15

Leu His Leu Pro Asn Leu Thr Glu Asp Gln Arg Ser Ala Phe Ile Gln
            20                  25                  30

Ser Leu Lys Asp Asp Pro Ser Val Ser Lys Glu Ile Leu Gly Glu Ala
        35                  40                  45
```

-continued

Lys Lys Leu Asn Asp Ala Gln Ala Pro Pro
        50                  55

<210> SEQ ID NO 79
<211> LENGTH: 58
<212> TYPE: PRT
<213> ORGANISM: Artificial Sequence
<220> FEATURE:
<223> OTHER INFORMATION: IB27

<400> SEQUENCE: 79

Ala Ala Ala Lys Phe Asp Glu Ala Gln Gln Ser Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Val Leu Gly Glu Ala
        35                  40                  45

Gln Lys Leu Asn Asp Ser Gln Ala Pro Lys
        50                  55

<210> SEQ ID NO 80
<211> LENGTH: 58
<212> TYPE: PRT
<213> ORGANISM: Artificial Sequence
<220> FEATURE:
<223> OTHER INFORMATION: IB24

<400> SEQUENCE: 80

Ala Ala Ala Gln His Asp Lys Glu Gln Gln Ser Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Lys
        50                  55

<210> SEQ ID NO 81
<211> LENGTH: 58
<212> TYPE: PRT
<213> ORGANISM: Artificial Sequence
<220> FEATURE:
<223> OTHER INFORMATION: IB26

<400> SEQUENCE: 81

Ala Ala Ala Gln His Asp Lys Asp Gln Gln Ser Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
        50                  55

<210> SEQ ID NO 82
<211> LENGTH: 58
<212> TYPE: PRT
<213> ORGANISM: Artificial Sequence
<220> FEATURE:
<223> OTHER INFORMATION: IB28

<400> SEQUENCE: 82

Ala Asp Ala Gln His Asp Glu Asp Gln Gln Ser Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Lys Asp Asp Pro Ser Gln Ser Lys Glu Ile Leu Gly Glu Ala
            35                  40                  45

Lys Lys Leu Asn Glu Ser Gln Ala Pro Lys
        50                  55

<210> SEQ ID NO 83
<211> LENGTH: 58
<212> TYPE: PRT
<213> ORGANISM: Artificial Sequence
<220> FEATURE:
<223> OTHER INFORMATION: IB20

<400> SEQUENCE: 83

Ala Asp Ala Lys Phe Asp Glu Ala Gln Gln Ser Ala Phe Tyr Glu Ile
1               5                   10                  15

Leu His Leu Pro Asn Leu Thr Glu Asp Gln Arg Asn Ala Phe Ile Gln
                20                  25                  30

Ser Leu Lys Asp Asp Pro Ser Thr Ser Lys Ser Leu Leu Gly Glu Ala
            35                  40                  45

Lys Lys Leu Asn Asp Ala Gln Ala Pro Pro
        50                  55

<210> SEQ ID NO 84
<211> LENGTH: 58
<212> TYPE: PRT
<213> ORGANISM: Artificial Sequence
<220> FEATURE:
<223> OTHER INFORMATION: domain C

<400> SEQUENCE: 84

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
                20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro Lys
        50                  55

<210> SEQ ID NO 85
<211> LENGTH: 58
<212> TYPE: PRT
<213> ORGANISM: Artificial Sequence
<220> FEATURE:
<223> OTHER INFORMATION: domain B

<400> SEQUENCE: 85

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 86
<211> LENGTH: 58
<212> TYPE: PRT
<213> ORGANISM: Artificial Sequence
<220> FEATURE:
<223> OTHER INFORMATION: domain Z

<400> SEQUENCE: 86

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 87
<211> LENGTH: 10
<212> TYPE: PRT
<213> ORGANISM: Artificial Sequence
<220> FEATURE:
<223> OTHER INFORMATION: spacer

<400> SEQUENCE: 87

Ala Ser Pro Ala Pro Ser Ala Pro Ser Ala
1               5                   10

<210> SEQ ID NO 88
<211> LENGTH: 21
<212> TYPE: PRT
<213> ORGANISM: Artificial Sequence
<220> FEATURE:
<223> OTHER INFORMATION: spacer and taq

<400> SEQUENCE: 88

Ala Ser Pro Ala Pro Ser Ala Pro Ser Ala Cys Ala Ser Trp Ser His
1               5                   10                  15

Pro Gln Phe Glu Lys
            20

<210> SEQ ID NO 89
<211> LENGTH: 8
<212> TYPE: PRT
<213> ORGANISM: Artificial Sequence
<220> FEATURE:
<223> OTHER INFORMATION: taq for purification

<400> SEQUENCE: 89

Trp Ser His Pro Gln Phe Glu Lys
1               5

<210> SEQ ID NO 90
<211> LENGTH: 58
<212> TYPE: PRT
<213> ORGANISM: Artificial Sequence
<220> FEATURE:
<223> OTHER INFORMATION: cs26 50C

<400> SEQUENCE: 90

Ile Ala Ala Gln His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Cys Leu Asn Asp Ala Gln Ala Pro Lys
    50                  55

<210> SEQ ID NO 91
<211> LENGTH: 58
<212> TYPE: PRT
<213> ORGANISM: Artificial Sequence
<220> FEATURE:
<223> OTHER INFORMATION: cs26 51C

<400> SEQUENCE: 91

Ile Ala Ala Gln His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Cys Asn Asp Ala Gln Ala Pro Lys
    50                  55

<210> SEQ ID NO 92
<211> LENGTH: 58
<212> TYPE: PRT
<213> ORGANISM: Artificial Sequence
<220> FEATURE:
<223> OTHER INFORMATION: cs26 53C

<400> SEQUENCE: 92

Ile Ala Ala Gln His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Cys Ala Gln Ala Pro Lys
    50                  55

<210> SEQ ID NO 93
<211> LENGTH: 58
<212> TYPE: PRT
<213> ORGANISM: Artificial Sequence
<220> FEATURE:
<223> OTHER INFORMATION: cs24 50C

<400> SEQUENCE: 93

Ile Ala Ala Gln His Asp Lys Glu Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Gly Glu Ala
        35                  40                  45

Lys Cys Leu Asn Asp Ala Gln Ala Pro Lys
    50                  55

<210> SEQ ID NO 94
<211> LENGTH: 58
<212> TYPE: PRT
<213> ORGANISM: Artificial Sequence
<220> FEATURE:

```
<223> OTHER INFORMATION: cs24 51C

<400> SEQUENCE: 94

Ile Ala Ala Gln His Asp Lys Glu Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Gly Glu Ala
        35                  40                  45

Lys Lys Cys Asn Asp Ala Gln Ala Pro Lys
    50                  55

<210> SEQ ID NO 95
<211> LENGTH: 58
<212> TYPE: PRT
<213> ORGANISM: Artificial Sequence
<220> FEATURE:
<223> OTHER INFORMATION: cs24 53C

<400> SEQUENCE: 95

Ile Ala Ala Gln His Asp Lys Glu Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Gly Glu Ala
        35                  40                  45

Lys Lys Leu Asn Cys Ala Gln Ala Pro Lys
    50                  55
```

FC BINDING PROTEINS WITH CYSTEINE IN THE C-TERMINAL HELICAL REGION

FIELD OF THE INVENTION

The present invention relates to Fc binding proteins comprising one or more domains having a Cysteine in the C-terminal helical region. The invention further relates to affinity matrices comprising the Fc binding proteins of the invention. The invention also relates to a use of these Fc binding proteins or affinity matrices for affinity purification of immunoglobulins and to methods of affinity purification using the Fc binding proteins of the invention.

BACKGROUND OF THE INVENTION

Many biotechnological and pharmaceutical applications require the removal of contaminants from a sample containing antibodies. An established procedure for capturing and purifying antibodies is affinity chromatography using the bacterial cell surface Protein A from *Staphylococcus aureus* as selective ligand for immunoglobulins (see, for example, review by Huse et al., J. Biochem. Biophys. Methods 51, 2002: 217-231). Wild-type Protein A binds to the Fc region of IgG molecules with high affinity and selectivity and is stable at high temperatures and in a wide range of pH values. Variants of Protein A with improved properties such as alkaline stability are available for purifying antibodies and various chromatographic matrices comprising Protein A ligands are commercially available. However, in particular wild-type Protein A based chromatography matrices show a loss of binding capacity for immunoglobulins following exposure to alkaline conditions.

TECHNICAL PROBLEMS UNDERLYING THE INVENTION

Most large scale production processes for antibodies or Fc-containing fusion proteins use Protein A for affinity purification. However, due to limitations of Protein A applications in affinity chromatography there is a need in the art to provide novel Fc binding proteins with improved properties that specifically bind to immunoglobulins in order to facilitate affinity purification of immunoglobulins. To maximally exploit the value of the chromatographic matrices comprising Fc binding proteins it is desirable to use the affinity ligand matrices multiple times. Between chromatography cycles, a thorough cleaning procedure is required for sanitization and removal of residual contaminants on the matrix. In this procedure, it is general practice to apply alkaline solutions with high concentrations of NaOH to the affinity ligand matrices. Wild-type Protein A domains cannot withstand such harsh alkaline conditions for an extended time and quickly lose binding capacity for immunoglobulin. Accordingly, there is an ongoing need in this field to obtain novel proteins capable of binding proteins comprising an Fc sequence.

The present invention provides Fc binding proteins that are particularly well-suited for affinity purification of immunoglobulins but overcome the disadvantages of the prior art. In particular, a significant advantage of the Fc binding proteins of the invention is their improved stability at high pH for a prolonged time period without reducing the Fc binding capacities in combination with high dynamic binding capacities. Further, the novel Fc binding proteins allow an elution of more than 95% at pH of 3.5 or higher of the bound Fc protein from the Fc binding protein immobilized to a matrix.

The above overview does not necessarily describe all problems solved by the present invention.

SUMMARY OF THE INVENTION

A first aspect of the present invention is to provide an Fc binding protein suitable for affinity purification. This is achieved with an Fc binding protein comprising one or more Fc binding domains, wherein at least the amino acid in position 43, 46, 47, 50, 51, or 53 corresponding to SEQ ID NO: 2 is Cysteine. In some embodiments, the Fc binding protein is comprising one or more Fc binding domains, wherein at least one domain comprises or essentially consists of or consists of an amino acid sequence of SEQ ID NO: 2 or an amino acid sequence with at least 89.5% identity thereto wherein at least the amino acid in position 43, 46, 47, 50, 51, or 53 corresponding to SEQ ID NO: 2 is Cysteine. In some embodiments, at least one domain comprises or essentially consists of or consists of an amino acid sequence of SEQ ID NOs: 3-16, or an amino acid sequence with at least 89.5% identity thereto, respectively, wherein at least the amino acid in position 43, 46, 47, 50, 51, or 53 corresponding to SEQ ID NOs: 3-16 is Cysteine. In some embodiments, at least one domain comprises or essentially consists of or consists of an amino acid sequence of SEQ ID NOs: 7-8, or an amino acid sequence with at least 89.5% identity thereto, respectively, wherein at least the amino acid in position 43, 46, 47, 50, 51, or 53 corresponding to SEQ ID NOs: 7-8 is Cysteine. In some embodiments, at least one domain comprises or essentially consists of or consists of an amino acid sequence selected from the group of SEQ ID NOs: 17-77, 90-95 or an amino acid sequence with at least 89.5% identity thereto.

In a second aspect the present invention relates to an affinity separation matrix comprising the Fc binding protein of the first aspect.

In a third aspect the present invention relates to a use of the Fc binding protein of the first aspect or of the affinity separation matrix of the second aspect for affinity purification of immunoglobulins or proteins comprising an Fc part of immunoglobulins.

In a fourth aspect the present invention relates to a method of affinity purification of immunoglobulins or proteins comprising an Fc part of immunoglobulins comprising the steps of (a) providing a liquid containing an immunoglobulin; (b) providing an affinity separation matrix comprising an immobilized Fc binding protein of the first aspect coupled to said affinity separation matrix; (c) contacting said liquid and said affinity separation matrix, wherein said immunoglobulin binds to said immobilized Fc binding protein; and (d) eluting said immunoglobulin from said matrix, thereby obtaining an eluate containing said immunoglobulin. This summary of the invention does not necessarily describe all features of the present invention. Other embodiments will become apparent from a review of the ensuing detailed description.

BRIEF DESCRIPTION OF THE FIGURES

FIG. 1. Amino acid sequences of Fc binding domains with Cysteine in the c-terminal helical region. The numbers in the top row refer to the corresponding amino acid position in the Fc binding domain. FIG. 1A. Fc binding domains of SEQ ID NO: 2. FIG. 1B. Examples for Fc binding domains with Cys in helix 3.

FIG. 2. Immobilization of Fc binding domains with Cysteine in the helix 3.

DETAILED DESCRIPTION OF THE INVENTION

Definitions

Figure 2A:
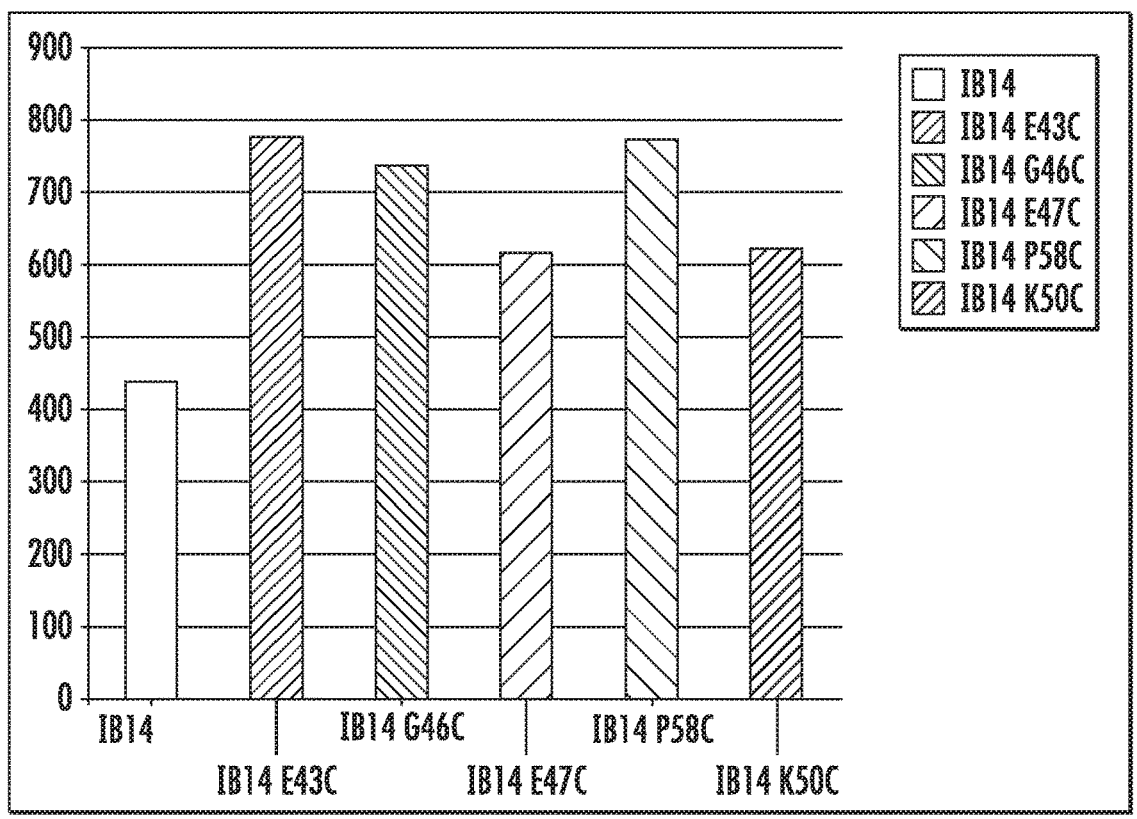
FIG. 2A. Coupling efficiency of IB14 proteins with Cysteine in positions 43, 46, 47, 50, or 58 on Expoxymatrix. Y-axis: coupled amount of protein in nmol/ml.

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

Preferably, the terms used herein are consistent with the definitions provided in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland). Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps.

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

The term "about", as used herein, encompasses the explicitly recited amounts as well as deviations therefrom of ±10%. More preferably, a deviation 5% is encompassed by the term "about".

Several documents (for example: patents, patent applications, scientific publications, manufacturer's specifications etc.) are cited throughout the text of this specification. Nothing herein is to be construed as an admission that the invention is not entitled to antedate such disclosure by virtue of prior invention. Some of the documents cited herein are characterized as being "incorporated by reference": In the event of a conflict between the definitions or teachings of such incorporated references and definitions or teachings recited in the present specification, the text of the present specification takes precedence.

All sequences referred to herein are disclosed in the attached sequence listing that, with its whole content and disclosure, is a part of this specification.

In the context of the present invention, the term "Fc binding protein" or "immunoglobulin-binding protein" or "Ig binding protein" is used to describe proteins that are capable to specifically bind to the Fc region of an immunoglobulin. The "immunoglobulin" as understood herein can include, but is not necessarily limited to, mammalian IgG, such as for example human $IgG_1$, human $IgG_2$, human $IgG_4$, mouse IgG, rat IgG, goat IgG, bovine IgG, guinea pig IgG, rabbit IgG; human IgM, human IgA; and immunoglobulin fragments comprising a Fc region. Due to a specific binding to the Fc region, the "Fc binding proteins" or "Ig binding proteins" of the invention are capable of binding to entire immunoglobulins, and to immunoglobulin fragments comprising a Fc region, fusion proteins comprising an Fc region of an immunoglobulin, and conjugates comprising an Fc region of an immunoglobulin. While the Fc binding proteins of the invention herein exhibit specific binding to the Fc region of an immunoglobulin, it is not excluded that Fc binding proteins can additionally bind with reduced affinity to other regions, such as Fab regions of immunoglobulins.

The term "binding" according to the invention preferably relates to a specific binding. "Specific binding" means that an Fc binding protein or an Fc binding domain binds stronger to an immunoglobulin for which it is specific compared to the binding to another non-immunoglobulin target.

The term "binding activity" refers to the ability of an Fc binding protein of the invention to bind to immunoglobulin. For example, the binding activity can be determined before and/or after alkaline treatment. The binding activity can be determined for an Fc binding protein or for an Fc binding protein coupled to a matrix, i.e. for an immobilized binding protein. The term "artificial" refers to an object that is not naturally occurring, i.e. the term refers to an object that has been produced or modified by man. For example, a polypeptide or polynucleotide sequence that has been generated by man (e.g. for example in a laboratory by genetic engineering, by shuffling methods, or by chemical reactions, etc.) or intentionally modified is artificial.

The term "dissociation constant" or "$K_D$" defines the specific binding affinity. As used herein, the term "$K_D$" (usually measured in "mol/L", sometimes abbreviated as "M") is intended to refer to the dissociation equilibrium constant of the particular interaction between a first protein and a second protein. In the context of the present invention, the term $K_D$ is particularly used to describe the binding affinity between an Fc binding protein and an immunoglobulin. An Fc binding protein of the invention is considered to bind to an immunoglobulin, if it has a dissociation constant $K_D$ to immunoglobulin of at least 1 μM or less, or preferably 100 nM or less, more preferably 50 nM or less, even more preferably 10 nM or less.

The terms "protein" and "polypeptide" refer to any linear molecular chain of two or more amino acids linked by peptide bonds and does not refer to a specific length of the product. Thus, "peptides", "protein", "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-translational modifications of the polypeptide, including without limitation glycosylation, acetylation, phosphorylation, amidation, proteolytic cleavage, modification by non-naturally occurring amino acids and similar modifications which are well-known in the art. Thus, Fc binding proteins comprising two or more protein domains also fall under the definition of the term "protein" or "polypeptides".

The terms "alkaline stable" or "alkaline stability" or "caustic stable" or "caustic stability" (also abbreviated as "cs" herein) refer to the ability of the Fc binding protein of the invention to withstand alkaline conditions without significantly losing the ability to bind to immunoglobulins. The skilled person in this field can easily test alkaline stability by incubating an Fc binding protein with sodium hydroxide solutions, e.g., as described in the Examples, and subsequent testing of the binding activity to immunoglobulin by routine experiments known to someone skilled in the art, for example, by chromatographic approaches.

Fc binding proteins of the invention as well as matrices comprising Fc binding proteins of the invention exhibit an "increased" or "improved" alkaline stability, meaning that the molecules and matrices incorporating said Fc binding proteins are stable under alkaline conditions for an extended period of time relative to a reference protein.

The term "parental" in the term "parental protein" or "parental domain" as used herein refers to an Fc binding protein that is subsequently modified to generate a variant of said parental protein or domain. Said parental protein or domain may be an artificial domain (for example, but not limited to, SEQ ID NO: 78-83), a naturally occurring *Staphylococcus aureus* Protein A domain (for example, SEQ ID NO: 84 for domain C, SEQ ID NO: 85 for domain B), or a variant or engineered version of a naturally occurring *Staphylococcus aureus* Protein A domain (for example, SEQ ID NO: 86 for domain Z).

The term "variant" as used herein includes an amino acid sequence of an Fc binding protein or domain that differs from another amino acid sequence by at least one amino acid substitution, deletion or insertion. These modifications may be generated by genetic engineering or by chemical synthesis or chemical reactions carried out by man. For example, SEQ ID NO: 27 (cs26 A460) is a variant of SEQ ID NO: 7 (cs26).

The term "conjugate" as used herein relates to a molecule comprising or essentially consisting of at least a first protein attached chemically to other substances such as to a second protein or a non-proteinaceous moiety.

The term "modification" or "amino acid modification" refers to an exchange, a deletion, or an insertion of an amino acid at a particular position in a parent polypeptide sequence by another amino acid. Given the known genetic code, and recombinant and synthetic DNA techniques, the skilled scientist can readily construct DNAs encoding the amino acid variants.

The term "substitution" or "amino acid substitution" refers to an exchange of an amino acid at a particular position in a parent polypeptide sequence by another amino acid. For example, the substitution G46C refers to a Fc binding protein, in which the glycine at position 46 is replaced by a cysteine. For the preceding example, 46C refers to a cysteine at position 46. For the purposes herein, multiple substitutions are typically separated by a slash. For example, A1I/S11A/K35R/A46C refers to a variant comprising the combination of substitutions A1I, S11A, K35R, and A46O.

The term "deletion" or "amino acid deletion" refers to the removal of an amino acid at a particular position in a parent polypeptide sequence.

The term "insertions" or "amino acid insertion" refers to the addition of amino acids to the parent polypeptide sequence.

Figure 1B:
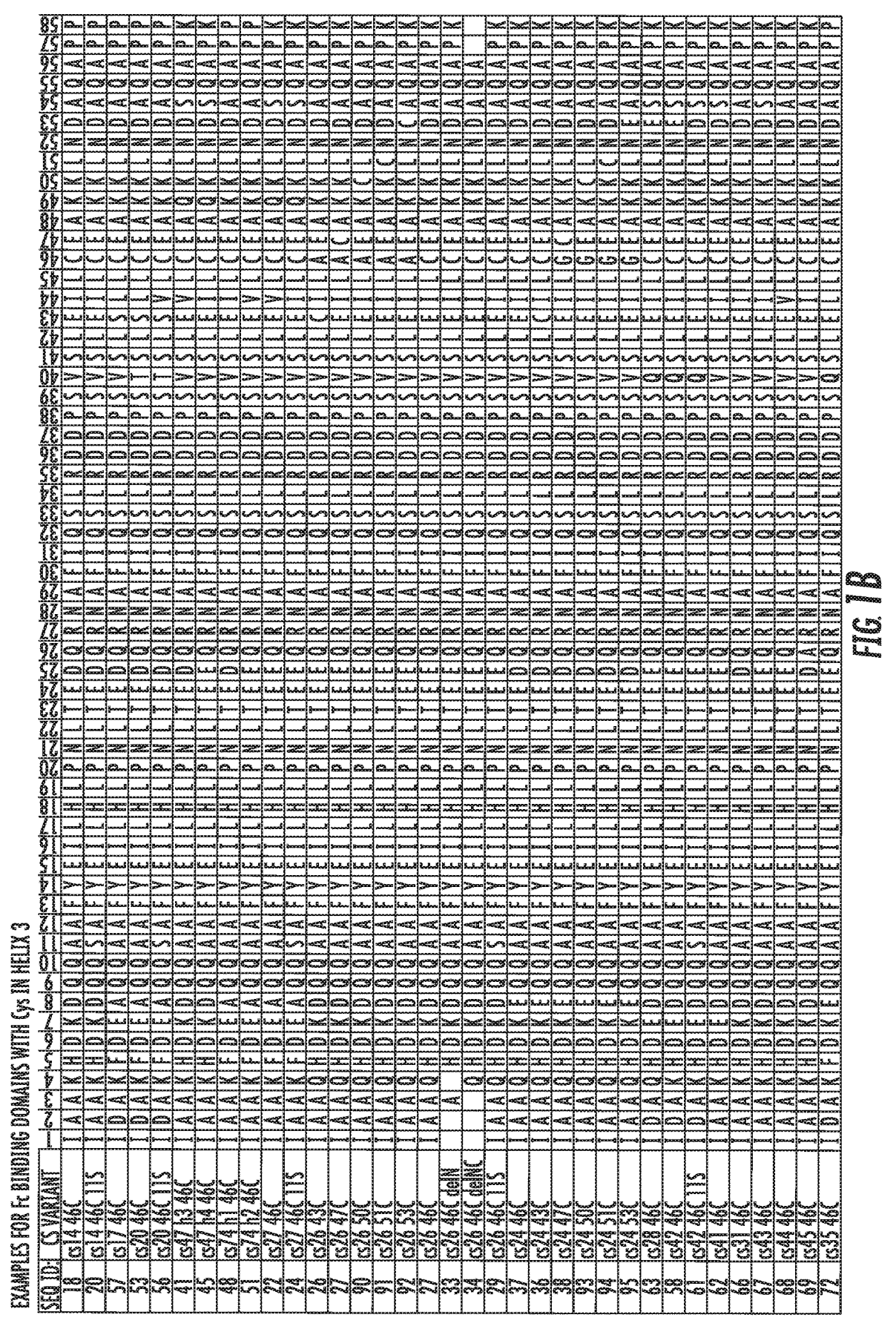

Throughout this description, the amino acid residue position numbering convention of FIG. 1 is used, and the position numbers are designated as corresponding to those for example in SEQ ID NOs: 1-16.

The term "amino acid sequence identity" refers to a quantitative comparison of the identity (or differences) of the amino acid sequences of two or more proteins. "Percent (%) amino acid sequence identity" or "percent identical" or ""percent identity" with respect to a reference polypeptide sequence is defined as the percentage of amino acid residues in a sequence that are identical with the amino acid residues in the reference polypeptide sequence, after aligning the sequences and introducing gaps, if necessary, to achieve the maximum percent sequence identity.

To determine the sequence identity, the sequence of a query protein is aligned to the sequence of a reference protein. Methods for alignment are well-known in the art. For example, for determining the extent of an amino acid sequence identity of an arbitrary polypeptide relative to a reference amino acid sequence, the SIM Local similarity program is preferably employed (Xiaoquin Huang and Webb Miller (1991), Advances in Applied Mathematics, vol. 12: 337-357), that is freely available (see also: http://www.expasy.org/tools/sim-prot.html). For multiple alignment analysis ClustalW is preferably used (Thompson et al. (1994) Nucleic Acids Res., 22(22): 4673-4680). Preferably, the default parameters of the SIM Local similarity program or of ClustalW are used, when calculating sequence identity percentages.

In the context of the present invention, the extent of sequence identity is generally calculated with respect to the total length of the unmodified sequence, if not explicitly stated otherwise. Each amino acid of the query sequence that differs from the reference amino acid sequence at a given position is counted as one difference. The sum of differences is then related to the length of the reference sequence to yield a percentage of non-identity. The quantitative percentage of identity is calculated as 100 minus the percentage of non-identity.

As used herein, the phrases "percent identical" or "percent (%) amino acid sequence identity" or "percent identity", in the context of two polypeptide sequences, refer to two or more sequences or subsequences that have in some embodiments at least about 80%, in some embodiments at least 82%, in some embodiments at least 84%, in some embodiments at least 86%, in some embodiments at least 87%, in some embodiments at least 89.5%, in some embodiments at least 91%, in some embodiments at least 93%, in some embodiments at least 94%, in some embodiments at least 96%, in in some embodiments at least 98%, and in some embodiments 100% amino acid residue identity, when compared and aligned for maximum correspondence, as measured using one of the following sequence comparison algorithms or by visual inspection. For clarity reasons, for example a sequence with at least 89.5% identity includes all sequences with identities higher than 89.5% identity, e.g. embodiments with at least 91%, at least 93%, at least 94%, at least 96%, at least 98%, 100% amino acid identity.

The percent identity exists in some embodiments over a region of at least 50 residue, at least 52 residues, in some embodiments over a region of at least 53 residues, in some embodiments over a region of at least 54 residues, in some embodiments over a region of at least 55 residues, in some embodiments over a region of at least 56 residues, in some embodiments over a region of at least 57 residues, and in some embodiments over a region of at least 58 residues.

The term "fused" means that the components are linked by peptide bonds, either directly or via peptide linkers.

The term "fusion protein" relates to a protein comprising at least a first protein joined genetically to at least a second protein. A fusion protein is created through joining of two or more genes that originally coded for separate proteins. Thus, a fusion protein may comprise a multimer of identical or different proteins which are expressed as a single, linear polypeptide As used herein, the term "linker" refers in its broadest meaning to a molecule that covalently joins at least two other molecules. In typical embodiments of the present invention, a "linker" is to be understood as a moiety that connects an Fc binding domain with at least one further Fc binding domain, i.e. a moiety linking two protein domains to each other to generate a multimer. In preferred embodiments, the "linker" is a peptide linker, i.e. the moiety linking the two protein domains is one single amino acid or a peptide comprising two or more amino acids.

The term "chromatography" refers to separation technologies which employ a mobile phase and a stationary phase to separate one type of molecules (e.g., immunoglobulins) from other molecules (e.g. contaminants) in the sample. The liquid mobile phase contains a mixture of molecules and transports these across or through a stationary phase (such as a solid matrix). Due to the differential interaction of the different molecules in the mobile phase with the stationary phase, molecules in the mobile phase can be separated.

The term "affinity chromatography" refers to a specific mode of chromatography in which a ligand coupled to a stationary phase interacts with a molecule (i.e. immunoglobulin) in the mobile phase (the sample) i.e. the ligand has a specific binding affinity for the molecule to be purified. As understood in the context of the invention, affinity chromatography involves the addition of a sample containing an immunoglobulin to a stationary phase which comprises a chromatography ligand, such as an Fc binding protein of the invention.

The terms "solid support" or "solid matrix" are used interchangeably for the stationary phase. The terms "affinity matrix" or "affinity separation matrix" or "affinity chromatography matrix", as used interchangeably herein, refer to a matrix, e.g. a chromatographic matrix, onto which an affinity ligand e.g., an Fc binding protein of the invention is attached. The ligand (e.g., Fc binding protein) is capable of specific binding to a molecule of interest (e.g., an immunoglobulin as defined above) which is to be purified or removed from a mixture.

The term "affinity purification" as used herein refers to a method of purifying immunoglobulins as defined above from a liquid by binding the immunoglobulins as defined above to an Fc binding protein that is immobilized to a matrix. Thereby, all other components of the mixture except immunoglobulins are removed. In a further step, the bound immunoglobulins is eluted in purified form.

EMBODIMENTS OF THE INVENTION

The present invention will now be further described. In the following passages different aspects of the invention are defined in more detail. Each aspect defined below may be combined with any other aspect or aspects unless clearly indicated to the contrary. In particular, any feature indicated as being preferred or advantageous may be combined with any other feature or features indicated as being preferred or advantageous.

In a first aspect the present invention is directed to a Fc binding protein, wherein the amino acid in position 43, the amino acid in position 46, the amino acid in position 47, the amino acid in position 50, the amino acid in position 51, or the amino acid in position 53 corresponding to SEQ ID NO: 2 is Cysteine. In a first aspect, the Fc protein comprises one or more domains, wherein at least one domain comprises or essentially consists of or consists of an amino acid sequence of SEQ ID NO: 2 or an amino acid with at least 80%, at least 81%, at least 82%, at least 84%, at least 86%, at least 87%, at least 89.5%, at least 91%, at least 93%, at least 94%, at least 96%, at least 98%, or 100% identity wherein the amino acid in position 43, the amino acid in position 46, the amino acid in position 47, the amino acid in position 50, the amino acid in position 51, or the amino acid in position 53 corresponding to SEQ ID NO: 2 is Cysteine.

The surprising advantage of the Fc binding proteins having a Cysteine in position 43, 46, 47, 50, 51, or 53 is that they confer an alkali stability for a prolonged period of time, without impairing the Fc-binding properties, and with site directed coupling efficiencies to a matrix providing a high binding capacity. The Fc binding domains of the invention are three-helix bundles of 58 amino acids with helix 1 from amino acid residues 7-19, helix 2 from amino acid residues 23-37, and helix 3 from amino acid residues 40-55. Amino acid positions 43, 46, 47, 50 and 51 are part of helix 3 of the Fc-binding protein while Fc binding is mediated by helices one and two. The Fc binding proteins of the invention have less than a 20% reduction in binding capacity following an incubation in 0.5 M NaOH for at least 6 hours up to at least 72 hours. This feature is important for chromatography approaches with cleaning procedures using alkaline solutions with high NaOH concentrations to remove contaminants on the matrix so for example that the matrix can be used several times. Further, in addition to having high caustic stability, Fc binding proteins having Cys in helix 3 in position 43, 46, 47, 50, 51, or 53 show high coupling efficiencies. For example, the dynamic binding capacity of variants with Cys in for example position 46 is superior compared to recombinant Protein A (see FIG. 5).

Preferred Fc binding proteins with Cysteine in helix 3. Some embodiments relate to sequences with an amino acid selected from the group consisting of SEQ ID NOs: 1-83. Some embodiments relate to amino acid sequences with at least 80%, at least 81%, at least 82%, at least 84%, at least 86%, at least 87%, at least 89.5%, at least 91%, at least 93%, at least 94.5%, at least 96%, at least 98%, or 100% sequence identity to an amino acid selected from the group consisting of SEQ ID NOs: 1-86, 90-95 provided that they have a Cysteine in position 43, 46, 47, 50, 51, or 53. Preferred are embodiments with sequences with at least 89.5% identity to an amino acid selected from the group consisting of SEQ ID NOs: 1-86, 90-95 having a Cysteine in position 43, 46, 47, 50, 51, or 53, preferably in position 43 or 46, more preferably in position 46.

The amino acid sequences of SEQ ID NOs: 1-86, 90-95 might comprise further modifications, such as insertions, deletions, or further substitutions. In some embodiments, Fc binding domains have 1, 2, 3, 4, 5, or 6 further substitutions. In some embodiments, Fc binding domains have a deletion of 1, 2, 3, or 4 amino acids within the first 4 amino acids of its N-terminus and/or a deletion of 1 or 2 amino acids at the C-terminus. In some embodiments, Fc binding domains have deletions at the N-terminus, for example in positions 1, 2, and 4, or in positions 1, 2, and 3. In some embodiments, Fc binding domains have deletions at the C-terminus, for example in positions 57 and/or 58 (as shown for example, but not limited to, SEQ ID NOs: 33-34). Some embodiments relate to amino acid sequences with at least 89.5% sequence identity to the amino acid sequence to any of the aforementioned SEQ ID NOs (for example but not limited to SEQ ID NOs: 1-86, 90-95). Examples for Fc binding domains with Cys in position 43, 46, 47, 50, 51, or 53 include for example but are not limited to the amino acid sequences shown in FIG. 1.

SEQ ID NO: 7 (cs26) and variants. In some embodiments, the Fc binding protein is comprising one or more domains of an amino acid sequence of SEQ ID NO: 7 or of an amino acid sequence with at least 89.5% identity thereto. For example, amino acid sequences with at least 89.5% identity to SEQ ID NO: 7 include but are not limited to cs24 (SEQ ID NO: 8). Examples for variants of cs26 having Cys in position 43, 46, 47, 50, 51, or 53 include for example but are not limited to SEQ ID NOs: 26-39, 90-95.

SEQ ID NO: 8 (cs24) and variants. In some embodiments, the Fc binding protein is comprising one or more domains of an amino acid sequence of SEQ ID NO: 8 or of an amino acid sequence with at least 89.5% identity thereto. For example, amino acid sequences with at least 89.5% identity to SEQ ID NO: 8 include but are not limited to cs26 (SEQ ID NO: 7). Examples for variants of cs24 having Cys in position 43, 46, 47, 50, 51, or 53 include for example but are not limited to SEQ ID NOs: 26-39, 90-95.

SEQ ID NO: 3 (cs14) and variants. In some embodiments, the Fc binding protein is comprising one or more domains of an amino acid sequence of SEQ ID NO: 3 or of a sequence with at least 89.5% sequence identity thereto suitable for modifications in position 43, 46, 47, 50, 51, or 53 with Cysteine. For example, amino acid sequences with at least 89.5% identity to SEQ ID NO: 3 include but are not limited to SEQ ID NO: 10 (cs25), SEQ ID NOs: 11 (cs47h3), SEQ ID NO: 12 (cs47h4), SEQ ID NO: 13 (cs74h1), and SEQ ID NO: 14 (cs74h2). Examples for variants of cs14 having Cys in position 43, 46, 47, 50, 51, or 53 include for example but are not limited to SEQ ID NOs: 17-20, 40-52, 64, 65, 70, 71, 74-76.

SEQ ID NO: 4 (cs27) and variants. In some embodiments, the Fc binding protein is comprising one or more domains of an amino acid sequence of SEQ ID NO: 4 or of an amino acid sequence with at least 89.5% identity thereto suitable for modifications in position 43, 46, 47, 50, 51, or 53 with Cysteine. Examples for variants of cs27 having Cys in position 43, 46, 47, 50, 51, or 53 include for example but are not limited to SEQ ID NOs: 21-25.

SEQ ID NO: 5 (cs20) and variants. In some embodiments, the Fc binding protein is comprising one or more domains of an amino acid sequence of SEQ ID NO: 5 or of an amino acid sequence with at least 89.5% identity thereto suitable for modifications in position 43, 46, 47, 50, 51, or 53 with Cysteine. For example, amino acid sequences with at least 89.5% identity to SEQ ID NO: 5 include but are not limited to SEQ ID NO: 9 (cs17). Examples for variants of cs20 having Cys in position 43, 46, 47, 50, 51, or 53 include for example but are not limited to SEQ ID NOs: 53-57.

SEQ ID NO: 6 (cs42) and variants. In some embodiments, the Fc binding protein is comprising one or more domains of an amino acid sequence of SEQ ID NO: 6 or of an amino acid sequence with at least 89.5% identity thereto suitable for modifications in position 43, 46, 47, 50, 51, or 53 with Cysteine. For example, amino acid sequences with at least 89.5% identity to SEQ ID NO: 16 include but are not limited to cs28 (different in position 4) or cs41 (SEQ ID NO: 15). Examples for variants of cs42 having Cys in position 43, 46, 47, 50, 51, or 53 include for example but are not limited to SEQ ID NOs: 58-63.

SEQ ID NO: 16 (cs43) and variants. In some embodiments, the Fc binding protein is comprising one or more domains of an amino acid sequence of SEQ ID NO: 16 or of an amino acid sequence with at least 89.5% identity thereto suitable for modifications in position 43, 46, 47, 50, 51, or 53 with Cysteine. For example, amino acid sequences with at least 89.5% identity to SEQ ID NO: 16 include but are not limited to cs44 (different in position 44), cs31 (different in positions 25 and 54), or cs45 (different in positions 25 and 26). Examples for variants of cs43 with Cys in position 43, 46, 47, 50, 51, or 53 include for example but are not limited to SEQ ID NOs: 66-69, 72.

Sequences of Fc Binding Proteins; Preferred Amino Acid Positions.

Surprisingly, a Cysteine in helix 3, particularly in amino acid positions selected from the group consisting of positions 43, 46, 47, 50, 51, or 53 of Fc binding domains increases the alkaline stability of Fc binding domain compared to a domain without Cysteine in position 43, 46, 47, 50, 51, or 53 as shown in the Figures and in the Examples, and improves the site-specific coupling of the Fc binding protein to a matrix which improves capacity.

In some embodiments, said Fc binding domain comprises an Isoleucine at position 1. It is preferred that the amino acid in position 1 of the Fc binding domain is not Threonine (T). It is preferred that the amino acid in position 1 is Isoleucine (I) or Alanine (A). Alternatively, position 1 may be deleted. In some embodiments, said Fc binding domain comprises an Alanine (A), Glutamic Acid (E), or Isoleucine (I) at position 11. It is preferred that the amino acid in position 11 is not Asparagine (N) or Lysine (K). It is preferred that the amino acid in position 11 is Alanine (A), Isoleucine (I), Glutamic acid (E), Histidine (H), or Proline (P), more preferred A, I, or E, most preferred A. Alternatively, the amino acid in position 11 is Serine (S). In some embodiments, said Fc binding domain comprises an Arginine (R) or Isoleucine (I) at position 35. It is preferred that the amino acid in position 35 is not Proline (P), Asparagine (N), Glycine (G), Tryptophan (W), Alanine (A), Glutamine (Q), or Methionine (M). In some embodiment, said Fc binding domain comprises a Leucine (L) at position 42. It is preferred that the amino acid in position 42 is not Tyrosine (Y). In some embodiments, in addition to 43C, 46C, 47C, 50C, 51C, or 53C, the Fc binding domain comprises 2, 3 or 4 of the amino acid positions selected from the group consisting of 1I, 11A, 11S, 35R, and 42L. In some embodiments, at least 90% of positions 1I, 3A, 6D, 9Q, 10Q, 12A, 13F, 14Y, 15E, 16I, 17L, 18H, 19L, 20P, 21N, 22L, 23T, 24E, 26Q, 27R, 28N, 29A, 30F, 31I, 32Q, 33S, 34L, 36D, 37D, 38P, 39S, 41S, 42L, 45L, 48A, 52N, 55Q, 56A, 57P are identical in Fc binding domains of the invention. It is preferred that position 2 is A or D, position 4 is K or Q, position 5 is H or F, position 7 is K or E, position 8 is D, A or E, position 11 is A, S, I, or E, position 25 is D or E, position 35 is R or I, position 40 is V, T or Q, position 43 is E, S or C, position 44 is 1, V or L, position 46 is C, A or G, position 47 is E or C, position 49 is K or Q, position 50 is K or C, position 51 is L or C, position 53 is D or E or C, position 54 is A or S, and position 58 is P or K.

An Fc binding protein of the invention comprises one or more Fc binding domains that comprises or essentially consists or consists of the amino acid sequence of SEQ ID NO: 2 or at least 89.5% identical amino acid sequences thereto. The amino acid sequence SEQ ID NO: 2 is the following amino acid sequence: $IX_2AX_4X_5DX_7X_8QQX_{11}AFYEILHLPNLTEX_{25}$ $QRNAFIQSLX_{35}DDPSX_{40}SLX_{43}X_{44}LX_{46}X_{47}$ $AX_{49}X_{50}X_{51}NX_{53}X_{54}QAPX_{58}$ wherein the amino acid at position 1 is selected from I, or is deleted, the amino acid at position 2 ($X_2$) is selected from A or D, or is deleted, the amino acid at position 3 is selected from A, or is deleted, the amino acid at position 4 ($X_4$) is selected from K or Q, or is deleted, the amino acid at position 5 ($X_5$) is selected from H or F, the amino acid at position 7 ($X_7$) is selected from K or E, the amino acid at position 8 ($X_8$) is selected from D, A, or E, the amino acid at position 11 ($X_{11}$) is selected from A, S, I, or E, the amino acid at position 25 ($X_{25}$) is selected from D or E, the amino acid at position 35 ($X_{35}$) is selected from R or I, the amino acid at position 40 ($X_{40}$) is selected from Q, T, or V, the amino acid at position 43 ($X_{43}$) is selected from E, S, or C, the amino acid at position 44 ($X_{44}$) is selected from I, L, or V, the amino acid at position 46 ($X_{46}$) is selected from G, A or C, the amino acid at position 47 ($X_{47}$) is selected from E or C, the amino acid at position 49 ($X_{49}$) is selected from K or Q, the amino acid at position 50 ($X_{50}$) is K or C, the amino acid at position 51 ($X_{51}$) is L or C, the amino acid at position 53 ($X_{53}$) is selected from D, E or C, the amino acid at position 54 ($X_{54}$) is selected from A or S, the amino acid at position 57 is selected from P, or deleted, and the amino acid at position 58 ($X_{58}$) is selected from P or K, or deleted. Fc binding proteins of the invention have a cysteine in one of the following positions: 43, 46, 47, 50, 51, or 53. Selected examples for Fc binding domains of the invention include for example but are not limited to SEQ ID NOs: 17-73, 90-95.

High alkaline stability as result of Cysteine in the c-terminal region of Fc binding proteins. In some embodiments, Fc binding proteins with Cysteine in position 43, 46, 47, 50, 51, or 53 provide surprisingly particularly good alkaline stability of the Fc binding protein, as shown in the Examples and in the Figures. It was most surprising and unexpected that the Fc binding proteins with Cysteine in helix 3 are able to bind to Ig even after alkaline treatment for several hours. The alkaline stability of the Fc binding protein is determined by comparing the loss in Ig binding activity after at least 6 h incubation in 0.5 M NaOH (see FIG. 3). For example, the binding capacity of cs26 46C remains at least 20% higher than wildtype domain C after prolonged (for example, 36 h) incubation with 0.5 M NaOH (see FIG. 4).

Affinity to Immunoglobulin. All Fc binding proteins of the invention bind to Immunoglobulin with a dissociation constant $K_D$ preferably below 500 nM, or below 100 nM, even more preferably 10 nM or less. Methods for determining binding affinities of Fc binding proteins or domains, i.e. for determining the dissociation constant $K_D$, are known to a person of ordinary skill in the art and can be selected for instance from the following methods known in the art: Surface Plasmon Resonance (SPR) based technology, Biolayer interferometry (BLI), enzyme-linked immunosorbent assay (ELISA), flow cytometry, isothermal titration calorimetry (ITC), analytical ultracentrifugation, radioimmunoassay (RIA or IRMA) and enhanced chemiluminescence (ECL). Some of the methods are described further in the Examples. Typically, the dissociation constant $K_D$ is determined at 20° C., 25° C., or 30° C. If not specifically indicated otherwise, the $K_D$ values recited herein are determined at 22° C.+/−3° C. by surface plasmon resonance. In an embodiment of the first aspect, the Fc binding protein has a dissociation constant $K_D$ to human $IgG_1$ in the range between 0.1 nM and 100 nM, preferably between 0.1 nM and 50 nM.

Multimers. In one embodiment of the invention, the Fc binding protein comprises 1, 2, 3, 4, 5, 6, 7, or 8, preferably 2, 3, 4, 5, or 6, Fc binding domains linked to each other, i.e. the Fc binding protein can be, for example, a monomer, a dimer, a trimer, a tetramer, a pentamer, or a hexamer. A multimer may comprise two, three, four, or even more binding domains.

Multimers of the invention are fusion proteins generated artificially, generally by recombinant DNA technology well-known to a skilled person.

In some embodiments, the multimer is a homo-multimer, e.g. the amino acid sequences of all Fc binding domains of the Fc binding protein are identical.

A multimer may comprise two or more Fc binding domains, wherein said Fc binding domains preferably comprise or essentially consist of a sequence as described above, provided that they have a Cysteine in position 43, 46, 47, 50, 51, or 53.

For example, SEQ ID NO: 27 or SEQ ID NO: 22 were used to generate the homo-multimeric fusion constructs described herein in Example 1, see for example SEQ ID NO: 32, SEQ ID NO: 35, or SEQ ID NO: 25.

In some embodiments, the multimer is a hetero-multimer, e.g. at least one alkaline stable Fc binding domain has a different amino acid sequence than the other Fc binding domains within the immunoglobulin-binding protein.

Linker. In some embodiments of the first aspect, the one or more Fc binding domains are directly linked to each other. In other embodiments, the one or more Fc binding domains are linked to each other with one or more linkers. Preferred in these typical embodiments are peptide linkers. This means that the peptide linker is an amino acid sequence that connects a first Fc binding domain with a second Fc binding domain. The peptide linker is connected to the first Fc binding domain and to the second Fc binding domain by a peptide bond between the C-terminal and N-terminal ends of the domains, thereby generating a single, linear polypeptide chain. The length and composition of a linker may vary between at least one and up to about 30 amino acids. More specifically, a peptide linker has a length of between 1 and 30 amino acids; e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 amino acids. It is preferred that the amino acid sequence of the peptide linker is stable against caustic conditions and proteases. Linkers should not destabilize the conformation of the domains in the Fc binding protein. Well-known are linkers that comprise or consist of small amino acids such as glycine and serine. The linkers can be glycine-rich (e.g., more than 50% of the residues in the linker can be glycine residues). Also preferred are linkers that comprise further amino acids. Other embodiments of the invention comprise linkers consisting of alanine, proline, and serine. Other linkers for the fusion of proteins are known in the art and can be used. In some embodiments, the multimer of Fc binding proteins comprises one or more linkers connecting the Fc binding domains wherein the linker are identical or different.

Conjugation to a solid support. In some embodiments of the invention, the Fc binding protein is conjugated to a solid support. Cysteine in helix 3 in position 43, 46, 47, 50, 51, or 53 of the Fc binding domain comprises an attachment site for site-specific covalent coupling of the Fc binding protein to a solid support. Cysteine in position 43, 46, 47, 50, 51, or 53 enables specific chemical reactions with a reactive group of the solid phase or a linker between the solid phase and the protein, for example selected from N-hydroxysuccinimide, iodacetamide, maleimide, epoxy, or alkene groups.

In some embodiments of the invention, the Fc binding protein may also comprise additional amino acid residues at the N- and/or C-terminal end, such as for example an additional sequence with or without a tag at the N- and/or C-terminal end.

Affinity separation matrix. In another aspect the present invention is directed to an affinity separation matrix, comprising an Fc binding protein of the first aspect.

In preferred embodiments of the second aspect, the affinity separation matrix is a solid support. The affinity separation matrix comprises at least one Fc binding protein of the invention.

An affinity matrix is useful for separation of immunoglobulins and should retain the Ig binding property even after highly alkaline conditions as applied during cleaning processes. Such cleaning of matrices is essential for long-term repeated use of matrices.

Solid support matrices for affinity chromatography are known in the art and include for example but are not limited to, agarose and stabilized derivatives of agarose (e.g. Sepharose 6B, Praesto™Pure; CaptivA®, rPROTEIN A Sepharose Fast Flow, Mabselect®, PrismA®, and other), cellulose or derivatives of cellulose, controlled pore glass (e.g. ProSep® vA resin), monolith (e.g. CIM® monoliths), silica, zirconium oxide (e.g. CM Zirconia or) CPG®, titanium oxide, or synthetic polymers (e.g. polystyrene such as Poros 50A or Poros MabCapture® A resin, polyvinylether, polyvinyl alcohol, polyhydroxyalkyl acrylates, polyhydroxyalkyl methacrylates, polyacrylamides, polymethacrylamides etc) and hydrogels of various compositions. In certain embodiments the support comprises a polyhydroxy polymer, such as a polysaccharide. Examples of polysaccharides suitable for supports include but are not limited to agar, agarose, dextran, starch, cellulose, pullulan, etc, and stabilized variants of these.

The formats for solid support matrices can be of any suitable well-known kind. Such solid support matrix for coupling the Fc binding protein of the invention might comprise for example, one of the following: columns, capillaries, particles, membranes, filters, monoliths, fibers, pads, gels, slides, plates, cassettes, or any other format commonly used in chromatography and known to someone skilled in the art.

In one embodiment, the matrix is comprised of substantially spherical particles, also known as beads, for example Sepharose or Agarose beads. Suitable particle sizes may be in the diameter range of 5-500 µm, such as 10-100 µm, such as 20-80 µm, such as 40-70 µm. Matrices in particle form can be used as a packed bed or in a suspended form including expanded beds. In an alternative embodiment, the solid support matrix is a membrane, for example a hydrogel membrane. In some embodiments, the affinity purification involves a membrane as matrix to which the Fc binding protein of the first aspect is covalently bound. The solid support can also be in the form of a membrane in a cartridge.

In some embodiments, the affinity purification involves a chromatography column containing a solid support matrix to which the Fc binding protein of the first aspect is covalently bound.

The Fc binding protein of the invention may be attached to a suitable solid support matrix via conventional coupling techniques. Methods for immobilization of protein ligands to solid supports are well-known in this field and easily performed by the skilled person in this field using standard techniques and equipment.

Use of the Fc binding protein. In a third aspect the present invention is directed to the use of the Fc binding protein of the first aspect or an affinity matrix of the second aspect for affinity purification of immunoglobulins or variants thereof, i.e. the Fc binding protein of the invention is used for affinity chromatography. In some embodiments, the Fc binding protein of the invention is immobilized onto a solid support as described in the second aspect of the invention.

Method of affinity purification of immunoglobulins. In a fourth aspect the present invention is directed to a method of affinity purification of immunoglobulins, the method comprising (a) providing a liquid containing an immunoglobulin; (b) providing an affinity separation matrix comprising an immobilized Fc binding protein of the first aspect coupled to said affinity separation matrix; (c) contacting said liquid with said affinity separation matrix, wherein said immunoglobulin binds to said immobilized Fc binding protein; and (d) eluting said immunoglobulin from said matrix, thereby obtaining an eluate containing said immunoglobulin. In some embodiments, the method of affinity purification may further comprising one or more washing steps carried out between steps (c) and (d) under conditions sufficient to remove from the affinity separation matrix some or all molecules that are non-specifically bound thereto. Non-specifically bound means any binding that does not involve an interaction between the at least one binding domain of the presently disclosed subject matter and an Immunoglobulin.

Affinity separation matrixes suitable for the disclosed uses and methods are those matrixes according to the embodiments described above and as known to someone skilled in the art.

In some embodiments of the fourth aspect, the elution of the immunoglobulin from the matrix in step (d) is effected through a change in pH and/or a change in salt concentration. Any suitable solution can be used, for example by a solution with pH 5 or lower (see e.g. Table 3 in Example 9), or by a solution with pH 11 or higher.

In some embodiments, a further step (f) for efficient cleaning and sanitization of the affinity matrix is added, preferably by using an alkaline liquid, for example, with pH of 13-14. In certain embodiments, the cleaning liquid comprises 0.1-1.0 M NaOH or KOH, preferably 0.25-0.5 M NaOH or KOH. Due to the high alkaline stability of the Fc binding proteins of the invention, such strong alkaline solution can be used for cleaning purposes.

In some embodiments, the affinity matrix can be re-used at least 10 times, at least 20 times, at least 30 times, at least 40 times, at least 50 times, at least 60 times, at least 70 times, at least 80 times, at least 90 times, or at least 100 times, due to a repetition of steps (a) to (e), optionally (a) to (f) can be repeated at least 10 times, at least 20 times, at least 30 times, at least 40 times, at least 50 times, at least 60 times, at least 70 times, at least 80 times, at least 90 times, or at least 100 times.

In general, suitable conditions for performing the method of affinity purification are well known to someone skilled in the art. In some embodiments, the disclosed uses or methods of affinity purification comprising the disclosed Fc binding domains may provide elution of at least about 90%, at least about 95%, at least about 96%, at least about 97%, at least about 98%, at least about 99% of Fc containing proteins at a pH of greater than or equal to 3.5 (e.g., about 4.0, about 4.5, about 5.0, about 5.5, about 6.0, or about 6.5).

Nucleic acid molecule. In a fifth aspect, the present invention is directed to a nucleic acid molecule, preferably an isolated nucleic acid molecule, encoding a Fc binding protein of any embodiment disclosed above. In one embodiment, the present invention is directed to a vector comprising the nucleic acid molecule. A vector means any molecule or entity (e.g., nucleic acid, plasmid, bacteriophage or virus) that can be used to transfer protein coding information into a host cell. In one embodiment, the vector is an expression vector.

In a sixth aspect, the present invention is directed to an expression system which comprises a nucleic acid or a vector as disclosed above, for example a prokaryotic host cell, for example *E. coli*, or a eukaryotic host, for example yeast *Saccharomyces cerevisiae* or *Pichia pastoris* or mammalian cells such as CHO cells.

Method for the production of a Fc binding protein. In a seventh aspect the present invention is directed to a method for the production of a Fc binding protein of the invention, comprising the step(s): (a) culturing the host cell of the sixth aspect under suitable conditions for the expression of the binding protein in order to obtain said Fc binding protein; and (b) optionally isolating said Fc binding protein. Suitable conditions for culturing a prokaryotic or eukaryotic host are well-known to the person skilled in the art.

Fc binding molecules of the invention may be prepared by any of the many conventional and well-known techniques such as plain organic synthetic strategies, solid phase-assisted synthesis techniques or by commercially available automated synthesizers. On the other hand, they may also be prepared by conventional recombinant techniques alone or in combination with conventional synthetic techniques.

One embodiment of the present invention is directed to a method for the preparation of a Fc binding protein according to the invention as detailed above, said method comprising the following steps: (a) preparing a nucleic acid encoding an Fc binding protein as defined above; (b) introducing said nucleic acid into an expression vector; (c) introducing said expression vector into a host cell; (d) cultivating the host cell; (e) subjecting the host cell to culturing conditions under which an Fc binding protein is expressed, thereby (e) producing an Fc binding protein as described above; optionally (f) isolating the protein produced in step (e); and (g) optionally conjugating the protein to solid matrices as described above.

In a further embodiment of the present invention the production of the Fc binding protein is performed by cell-free in vitro transcription/translation.

EXAMPLES

The following Examples are provided for further illustration of the invention. The invention, however, is not limited thereto, and the following Examples merely show the practicability of the invention on the basis of the above description.

Example 1. Generation of Artificial Mosaic Proteins that Bind to Fc

Fc binding proteins were initially generated by a shuffling process of naturally occurring Protein A domains (E, B, D, A, C, Z). In more detail, the shuffling process as understood herein is an assembly process resulting in artificial amino acid sequences starting from a set of non-identical known amino acid sequences. The shuffling process comprised the following steps: a) providing sequences of five naturally occurring Protein A domains E, B, D, A, and C, and Protein A variant domain Z; b) alignment of said sequences; c) statistical fragmentation in silico to identify subsequences that were recombined, and then d) assembly of new, artificial sequences of the various fragments to produce a mosaic product, i.e. a novel and artificial amino acid sequence. The fragments generated in step c) were of any length, e.g. if the fragmented parent sequence had a length of n, the fragments was of length 1 to n−1.

The relative positions of the amino acids in the mosaic products were maintained with respect to the starting amino acid sequences. At least 90% of positions Q9, Q10, A12, F13, Y14, L17, P20, L22, Q26, R27, F30, I31, Q32, S33, L34, D36, D37, P38, S39, S41, L45, E47, A48, K50, L51, Q55, A56, P57 are identical between the artificial amino acid sequences of for example IB14, IB27, IB24, IB26, IB28, IB20 (SEQ ID NOs: 78-83) and naturally occurring Protein A domains or Protein A domain variants. The overall amino acid sequence of, for example, Fc binding proteins IB14, IB26, and IB27 is artificial in that it is not more than 85% identical to the overall amino acid sequence of any of the naturally occurring Protein A domains or domain Z. After the initial artificial Fc binding proteins was generated, in some cases the protein was further modified by site-specific randomization of the amino acid sequence to further modify biochemical properties. The further modifications were introduced by site-saturation mutagenesis of individual amino acid residues.

Genes for artificial Fc binding proteins were synthesized and cloned into an *E. coli* expression vector using standard methods known to a skilled person. DNA sequencing was used to verify the correct sequence of inserted fragments.

To generate multimeric Fc binding proteins, 2 or 3 identical Fc binding domains were genetically fused.

For specific purification, optionally a strep-tag (WSHPQFEK; SEQ ID NO: 89) was added to the C-terminus of the Fc binding proteins.

Example 2. Mutagenesis to Generate Variants

For site-directed mutagenesis, the Q5® site-directed Mutagenesis Kit (NEB; Cat. No. E0554S) was used according to the manufacturer's instructions. PCRs were carried out with oligonucleotides coding for each specific substitution respectively and a plasmid containing the template. Products were ligated and transformed into *E. coli* XL2-blue cells (Stratagene) via electroporation. Single colonies were isolated and DNA sequencing was used for insert containing clones to verify the correct sequences.

A combination of several point mutations was generated by GeneArt™ Strings™ synthesis (Thermo Fisher Scientific). The Strings DNA fragments corresponded to a purified PCR product and were cloned into a derivate of a pET28a vector. Ligation products were transformed into *E. coli* XL2-blue cells via electroporation. Single colonies were screened by PCR to identify constructs containing inserts of the right size. DNA sequencing was used to verify the correct sequences. Some variants with point mutations are shown for example in FIG. 1.

Example 3. Expression of Fc Binding Proteins

BL21 (DE3) competent cells were transformed with an expression plasmid encoding Fc binding proteins. Cells were spread onto selective agar plates (Kanamycin) and incubated overnight at 37° C. Precultures were inoculated from single colony in 100 ml 2xYT medium and cultured for 16 hours at 37° C. at 160 rpm in a conventional orbital shaker in baffled 1 L Erlenmeyer flasks supplemented with 150 μg/ml Kanamycin without lactose and antifoam. The $OD_{600}$ readout should be in the range of 6-12. Main culture was inoculated from previous overnight culture with an adjusted start-$OD_{600}$ of 0.5 in 400 ml superrich medium (modified H15 medium 2% Glucose, 5% Yeast extract, 0.89% Glycerol, 0.76% Lactose, 250 mM MOPS, 202 mM TRIS, pH 7.4, Antifoam SE15) in 1 L thick-walled Erlenmeyer flasks that was supplemented with 150 μg/ml Kanamycin. Cultures were transferred to a resonant acoustic mixer (RAMbio) and incubated at 37° C. with 20×g. Aeration was facilitated by Oxy-Pump stoppers. Recombinant protein expression was induced by metabolizing glucose and subsequently allowing lactose to enter the cells. At pre-defined time points $OD_{600}$ was measured, samples adjusted to 5/$OD_{600}$ were withdrawn, pelleted and frozen at −20° C. Cells were grown overnight for approx. 24 hours to reach a final $OD_{600}$ of about 45-60. To collect biomass cells were centrifuged at 16000×g for 10 min at 20° C. Pellets were weighed (wet weight) and pH was measured in the supernatant. Cells were stored at −20° C. before processing.

Example 4: SDS-PAGE Analysis of Expression and Solubility of Fc Binding Proteins Samples taken during fermentation were resuspended in 300 μl extraction buffer (PBS supplemented with 0.2 mg/ml Lysozyme, 0.5× BugBuster, 7.5 mM $MgSO_4$, 40 U Benzonase) and solubilized by agitation in a thermomixer at 700 rpm, rt for 15 min. Soluble proteins were separated from insoluble proteins by centrifugation (16000×g, 2 min, rt). Supernatant was withdrawn (soluble fraction) and the pellet (insoluble fraction) was resuspended in equivalent amount of urea buffer (8 M urea, 0.2 M Tris, 2 mM EDTA, pH 8.5). 50 μl were taken both from the soluble and insoluble fraction, and 12 μl 5× sample buffer as well as 5 μl 0.5 M DTT were added. Samples were boiled at 95° C. for 5 min. Finally, 8 μl of those samples were applied to NuPage Novex 4-12% Bis-Tris SDS gels which were run in accordance to the manufacturer's recommendations and stained with Coomassie. High level expression of all Fc binding proteins was found under optimized conditions within the chosen period of time (data not shown). All expressed Fc binding proteins were soluble to more than 95% according to SDS-PAGE.

Example 5: Purification of Fc Binding Proteins

Fc binding proteins were expressed in the soluble fraction of *E. coli* with a C-terminal StrepTagII (WSHPQFEK). The cells were lysed by two freeze/thaw cycles and the purification step was performed with Strep-Tactin®-resin according to the manufacturer's instructions (IBA, Goettingen, Germany). To avoid disulfide formation the buffers were supplemented with 1 mM DTT.

Alternatively, Fc binding proteins were expressed in the soluble fraction of *E. coli* with a C-terminal StrepTagII. The cells were resuspended in cell disruption buffer and lysed by a constant cell disruption system (Unit F8B, Holly Farm Business Park) at 1 kbar for two cycles. Purification step was performed with Strep-Tactin resin (IBA, Goettingen, Germany) and additional gel filtration (Superdex 75 16/60; GE Healthcare) using an ÄKTAxpress system (Ge Healthcare) according to the manufacturer's instructions. To avoid disulfide formation buffers for Strep-Tactin-purification were supplemented with 1 mM DTT and citrate-buffer (20 mM Citrat, 150 mM NaCl, pH 6.0) was used as running buffer for gel filtration.

Example 6. The Fc Binding Proteins Bind to IgG with High Affinities (as Determined by ELISA)

The affinities of the Fc binding proteins towards $IgG_1$ or $IgG_2$ or $IgG_4$ were determined using an Enzyme Linked Immunosorbent Assay (ELISA). $IgG_1$ or $IgG_2$ or $IgG_4$ containing antibodies (e.g. Cetuximab for $IgG_1$, Panitumumab for $IgG_2$, or Natalizumab for $IgG_4$) were immobilized on a 96 well Nunc MaxiSorb ELISA plate (2 μg/ml). After incubation for 16 h at 4° C. the wells were washed three times with PBST (PBS+0.1% Tween 20) and the wells were blocked with 3% BSA in PBS (2 h at room temperature). The negative controls were wells blocked only with BSA. After blocking, the wells were washed three times with PBST and incubated for 1 h with the Fc binding protein (in PBST) at room temperature. After incubation the wells were washed three times with PBST and subsequently incubated with Strep-Tactin-HRP (1:10000) (IBA, Goettingen, Germany) for 1 h at room temperature. Afterwards the wells were washed three times with PBST and three times with PBS. The activity of the horseradish peroxidase was visualized by adding TMB-Plus substrate. After 30 min the reaction was stopped by adding 0.2 M $H_2SO_4$ and the absorbance was measured at 450 nm. For example, as determined via ELISA, the $K_D$ for human $IgG_1$ is 4.9 nM for IB14; 3.4 nM for domain Z; 3.1 nM for domain B; and 2.8 nM for domain C.

Example 7. The Fc Binding Proteins Bind to IgG with High Affinities (as Determined with Surface Plasmon Resonance Experiments)

A CM5 sensor chip (GE Healthcare) was equilibrated with SPR running buffer. Surface-exposed carboxylic groups were activated by passing a mixture of EDC and NHS to yield reactive ester groups. 700-1500 RU on-ligand were immobilized on a flow cell, off-ligand was immobilized on another flow cell. Injection of ethanolamine after ligand immobilization removes non-covalently bound Fc binding protein. Upon ligand binding, protein analyte was accumulated on the surface increasing the refractive index. This change in the refractive index was measured in real time and plotted as response or resonance units (RU) versus time. The analytes were applied to the chip in serial dilutions with a suitable flow rate (μl/min). After each run, the chip surface was regenerated with regeneration buffer and equilibrated with running buffer. The control samples were applied to the matrix. Regeneration and re-equilibration were performed as previously mentioned. Binding studies were carried out by the use of the Biacore® 3000 (GE Healthcare) at 25° C.; data evaluation was operated via the BIAevaluation 3.0 software, provided by the manufacturer, by the use of the Langmuir 1:1 model (RI=0). Evaluated dissociation constants ($K_D$) were standardized against off-target and $K_D$ values of different artificial Fc binding proteins for human $IgG_1$-Fc, Cetuximab ($IgG_1$), Natalizumab ($IgG_4$), or Panitumomab ($IgG_2$) are shown in Table 1.

TABLE 1

| | | $K_D$ values of Fc binding proteins for Ig | | | |
|---|---|---|---|---|---|
| Fc binding protein | SEQ ID NO: | Kd [nM] IgG-Fc | Kd [nM] $IgG_1$ | Kd [nM] $IgG_4$ | Kd [nM] $IgG_2$ |
| IB14 | 78 | 1.28 | | | |
| IB14 E43C | 74 | 45.5 | | | |
| IB14 G46C | 75 | 72.9 | | | |
| IB14 E47C | 76 | 48.8 | | | |
| IB14 K50C | 77 | 42.8 | | | |

TABLE 1-continued

K_D values of Fc binding proteins for Ig

| Fc binding protein | SEQ ID NO: | Kd [nM] IgG-Fc | Kd [nM] IgG$_1$ | Kd [nM] IgG$_4$ | Kd [nM] IgG$_2$ |
|---|---|---|---|---|---|
| cs14 | 3 | 6.48 | 2.9 | 2.51 | 7.42 |
| cs14 G46C | 18 | | 4.88 | 3.38 | 35.6 |
| cs14 E43C | 17 | | 0.453 | 0.302 | 1.75 |
| cs27 | 4 | | 3.64 | 2.54 | 21.6 |
| cs27 G46C | 22 | | 0.518 | 0.302 | 2.74 |
| cs26 | 7 | | 6.5 | 5.81 | 66.6 |
| cs26 A46C | 27 | | 5.75 | 3.00 | 101 |
| cs26 A46C (dimer) | 32 | | 2.59 | 1.86 | 20.5 |
| cs26 A46C (trimer) | 35 | | 2.23 | 1.98 | 13.3 |
| Domain C | 84 | | 4.91 | 3.95 | 58.1 |

Example 8. Fc Binding Proteins Coupled to an Epoxy-Activated Matrix (Sepharose 6B)

Figure 2B:
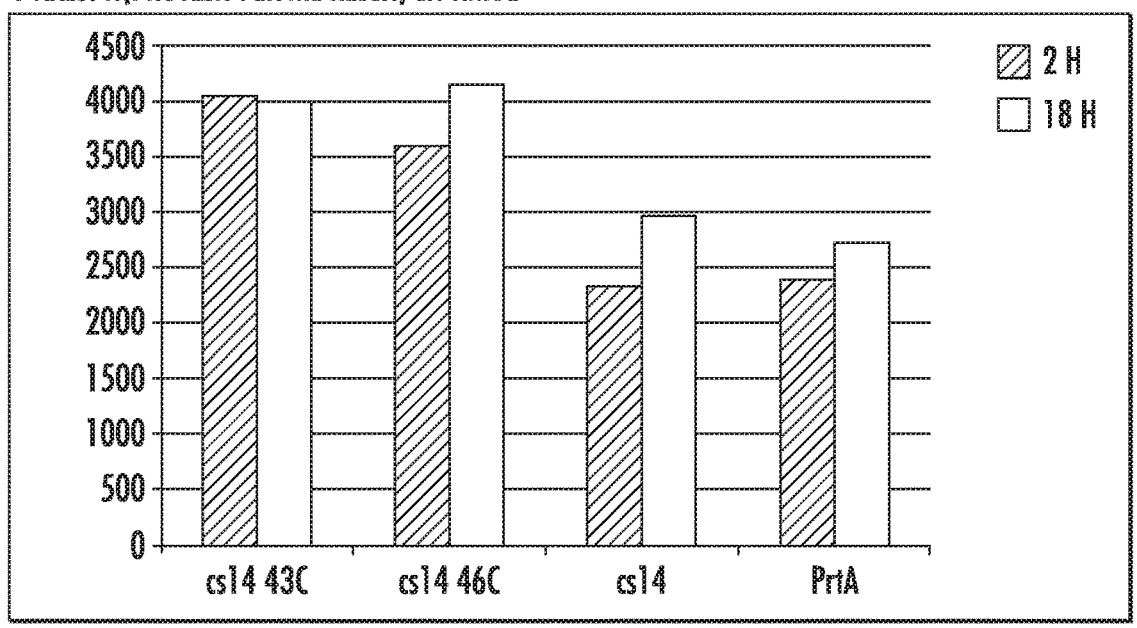
FIG. 2B. Coupling of cs14 43C and cs14 46C to Epoxy-activated Sepharose 6B matrix. Y-axis: n(protein per ml resin) in nmol FIG. 3. Caustic stability of Fc binding proteins with Cysteine in the c-terminal region 3.

Purified Fc binding proteins were coupled to epoxy-activated matrix (Sepharose 6B, GE; Cat. No. 17-0480-01) according to the manufacturer's instructions (coupling conditions: pH 9.0 overnight, blocking for 5 h with ethanolamine). Cetuximab was used as IgG sample (5 mg; 1 mg/ml matrix). Cetuximab was applied in saturated amounts to the matrix comprising immobilized Fc binding protein. The matrix was washed with 100 mM glycine buffer, pH 2.5 to elute Cetuximab that was bound to the immobilized IgG-binding protein. The concentration of the eluted IgG was measured by BLI (quantification with Protein A Octet-sensors and Cetuximab as standard) in order to determine the binding activity of the Fc binding proteins. FIG. 2A shows the the coupling efficiency of IB14 (SEQ ID NO: 78) and IB14 variants with Cystein in Positions 43, 46, 47, 50, or 58 (SEQ ID NOs: 74-77, respectively). The coupling efficiency of all IB14 variants with Cys in positions 43, 46, 47, 50, or 58 was higher than for IB14. FIG. 2B shows the coupling of cs14 46C (SEQ ID NO: 18) or cs14 43C (SEQ ID NO: 17) to Epoxy activated Sepharose 6B matrix compared to cs14 with an C-terminal Cys and compared to a commercially available Protein A. Coupling conditions were 450 μM, 4500 nmol/ml, pH 9, 2 h or 18 h at 30° C., 1 mM TCEP, 1 M (NH$_4$)$_2$SO$_4$. Only minor change in net coupling rate were observed between 2 h and 18 h. Coupling rates are shown in nmole (domain)/ml.

Figure 3A:
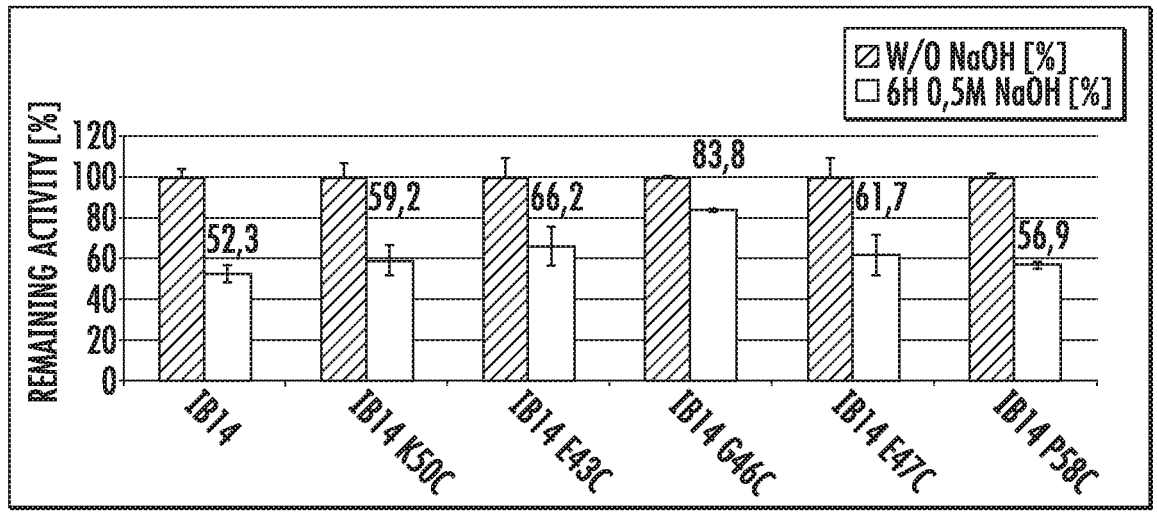
FIG. 3A. Analysis of the alkaline stability of IB14 with Cysteine in positions 43, 46, 47, 50, or 58. Y-axis: remaining IgG binding activity of the Fc binding protein IB14 and Cys Variants in %. Grey column: IgG binding activity after 6 h of continuous 0.5 M NaOH treatment. Black column: IgG binding activity without NaOH.
Figure 3B:
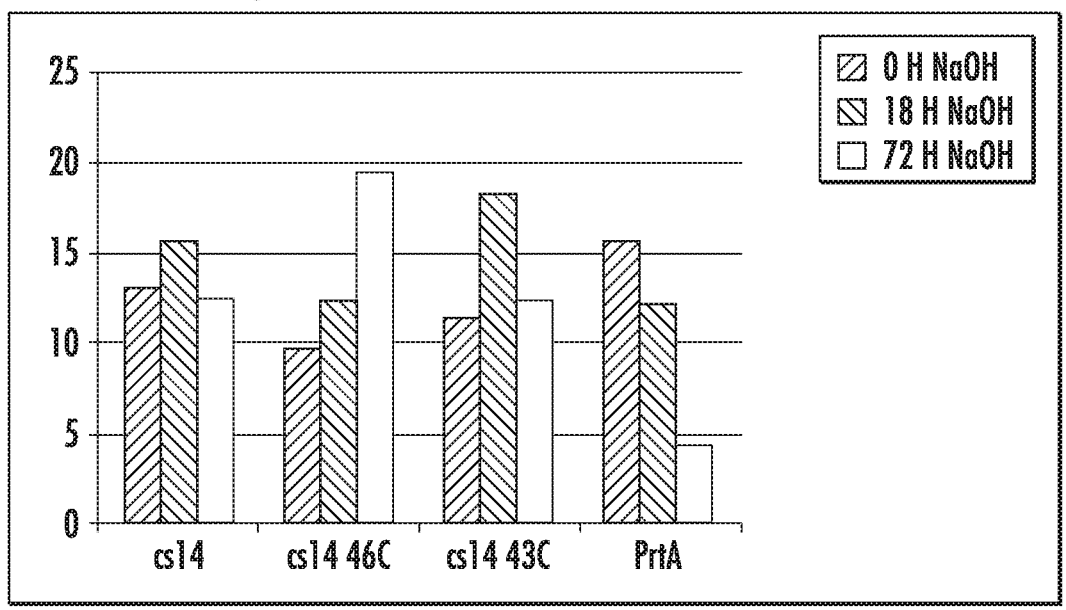
FIG. 3B. Caustic stability and DBC 10% of cs14 with Cysteine in positions 43 or 46. Y-axis: DBC 10% (mg/ml). Black: DBC 10% (mg/ml), 0 h NaOH, light grey: DBC 10% (mg/ml), 18 h NaOH, dark grey: DBC 10% (mg/ml), 72 h NaOH, The Cys variants were compared to cs14 with C-terminal Cysteine and to Protein A.
Figure 4:
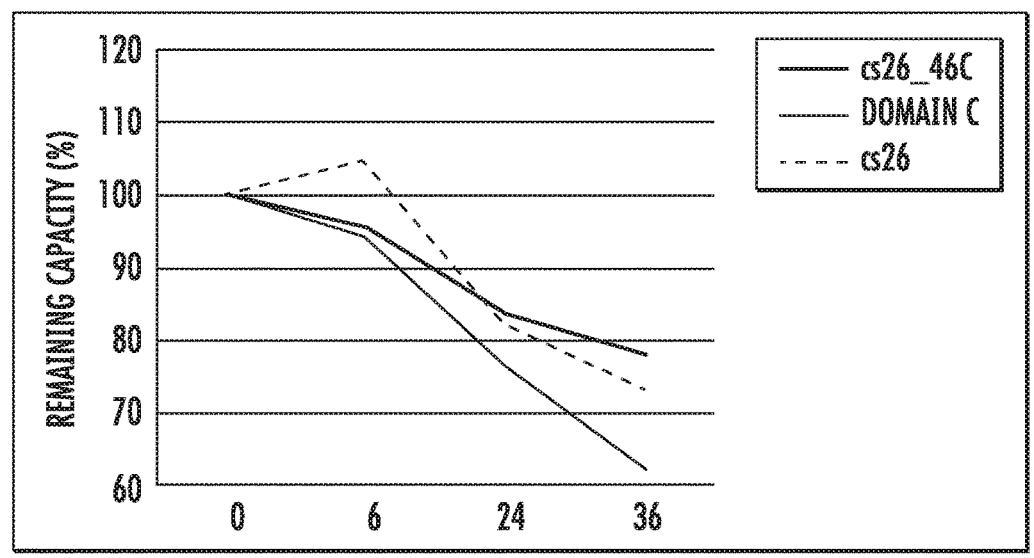
FIG. 4. The remaining binding capacity (in %) after 6, 24, and 36 hours of continuous 0.5 M NaOH treatment is shown for cs26 46C, compared to cs26 without Cys in position 46 and compared to wildtype Protein A domain C. The x-axis shows the time of 0.5 M NaOH incubation in hours.

Example 9. Alkaline Stability of Fc Binding Proteins Coupled to an Epoxy-Activated Matrix Columns were incubated with 0.5 M NaOH for 0 h, 6 h, 18 h, 24 h, 36 h, or 72 h at room temperature (22° C.+/−3° C.). The Ig binding activity of the immobilized proteins was analyzed before and after incubation with 0.5 M NaOH. The Ig binding activity of immobilized proteins before NaOH treatment was defined as 100%. The remaining IgG binding activity after continuous 0.5 M NaOH treatment for 6 hours is shown in FIG. 3A for IB14 variants (SEQ ID NOs: 74-77). FIG. 3B shows caustic stability after continuous 0.5 M NaOH treatment for 0 h, 18 h, or 72 h for cs14 46C, cs14 43C, cs14, and for a commercially available Protein A. The proteins were immobilized to Epoxy Sepharose for 2 h at 30° C. (4500 nmol/ml). The dynamic binding capacity DBC 10% was determined at 5 min residence time. Cs14 46C shows the highest DBC10% after 72 h of continuous 0.5 NaOH treatment for 19.5 mg/ml which is more than 20% more than the value measured for the commercially available Protein A. FIG. 4 shows the remaining binding capacity after continuous 0.5 M NaOH treatment for 6, 24, and 36 hours for cs26 46C (SEQ ID NO: 27) compared to cs26 (SEQ ID NO: 7) and to wildtype domain C (SEQ ID NO: 84). The binding capacitiy of cs26 A46C (monomer or dimer) remains >20% after at least after 36 h 0.5 M NaOH incubation, see Table 2.

TABLE 2

Caustic stability of cs26 A46C compared to cs26 and to wildtype domain C

| Fc binding protein | 0 h | 6 h | 24 h | 36 h | vs C @ 36 h |
|---|---|---|---|---|---|
| cs26 A46C | 100 | 95 | 83 | 78 | 42% |
| cs26 A46C (dimer) | 100 | 92 | 81 | 72 | 24.8% |
| cs26 | 100 | 105 | 82 | 73 | 27.7% |
| domain C | 100 | 95 | 76 | 62 | |

Example 10. Fc Binding Proteins Coupled to Agarose-Based Chromatography Beads Praesto™ Pure45

Purified Fc binding proteins were coupled to agarose-based chromatography beads (Praesto™ Pure45, Purolite; Cat. No. PR01262-166) according to the manufacturer's instructions (coupling conditions: pH 9.5, 3 hours, 35° C., 4.1 M NaSO$_4$, blocking overnight with ethanolamine). Polyclonal human IgG Gammanorm® (Ocatpharm) was used as IgG sample (conc. 2.2 mg/ml).

Figure 5:
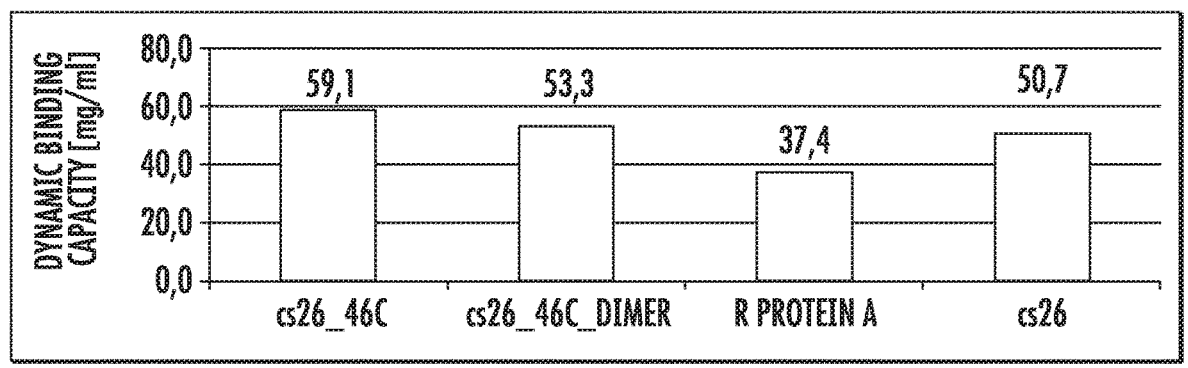
FIG. 5. The dynamic binding capacity (DBC; mg/ml) is shown for cs26 46C (monomer and dimer), compared to cs26 without Cys in position 46, and compared to recombinant wildtype Protein A.

Polyclonal hIgG sample was applied in saturated amounts to the matrix comprising immobilized Fc binding protein. The matrix was washed with 100 mM Citrate buffer, pH 2.0 to elute hIgG that was bound to the immobilized Fc binding protein. Dynamic binding capacity was determined for cs26 46C (monomer and dimer; (SEQ ID NOs: 27, 32) compared to recombinant wildtype Protein A by the mass of injected hIgG at 10% breakthrough at 6 min residence time. FIG. 5 shows that Cs26 46C has a 61.2% higher DBC at 6 min residence time than recombinant Protein A.

Example 11. Elution of IgG from Fc Binding Proteins Coupled to Agarose-Based Chromatography Beads Praesto™ Pure45 and/or Pure85

Purified Fc binding proteins (cs26 46C) were coupled to agarose-based chromatography beads (Praesto™ Pure45 or Pure 5) according to the manufacturer's instructions. Polyclonal human IgG Gammanorm® and monoclonal IgG$_1$ antibody Cetuximab was used as IgG sample (conc. 2.2 mg/ml), loading up to DBC10%. Polyclonal hIgG sample was applied in saturated amounts to the matrix comprising immobilized Fc binding protein. In a two-step process, the matrix was first washed with 100 mM Citrate buffer, pH 3.5 and then with 100 mM Citrate buffer, pH 2.0 to elute hIgG that was bound to the immobilized Fc binding protein. Table 3 shows that almost 100% of the bound IgG was eluted from beads coupled with cs26 46C at pH 3.5.

TABLE 3

Elution of IgG from cs26 46C coupled to beads

| Antibody | Eluted protein at 0.1M citrate pH 3.5 (%) | Eluted protein at 0.1M citrate pH 2.0 (%) | Recovery: Load/Elution (%) |
|---|---|---|---|
| Gammanorm | 99.8 | 0.2 | 85 |
| Cetuximab | 100 | 0 | 86 |

The invention claimed is:

1. An Fc binding protein comprising one or more domains, wherein at least one domain comprises an amino acid sequence of SEQ ID NO: 2 wherein the amino acid in position 43, the amino acid in position 46, the amino acid in position 47, the amino acid in position 50, the amino acid in position 51, or the amino acid in position 53 corresponding to SEQ ID NO: 2 is Cysteine.

2. An Fc binding protein of claim 1, wherein at least one domain comprises an amino acid sequence of SEQ ID NO: 3 or an amino acid sequence with at least 89.5% identity thereto wherein the amino acid in position 43, the amino acid in position 46, the amino acid in position 47, the amino acid in position 50, the amino acid in position 51, or the amino acid in position 53 corresponding to SEQ ID NO: 3 is Cysteine.

3. The Fc binding protein of claim 1, wherein at least one domain comprises an amino acid sequence of SEQ ID NOs: 3-16 or an amino acid sequence with at least 89.5% identity thereto, respectively, wherein the amino acid in position 43, the amino acid in position 46, the amino acid in position 47, the amino acid in position 50, the amino acid in position 51, or the amino acid in position 53 corresponding to SEQ ID NOs: 3-16 is Cysteine.

4. The Fc binding protein of claim 1, wherein at least one domain comprises an amino acid sequence of SEQ ID NOs: 7-8 or an amino acid sequence with at least 89.5% identity thereto, respectively, wherein the amino acid in position 43, the amino acid in position 46, the amino acid in position 47, the amino acid in position 50, the amino acid in position 51, or the amino acid in position 53 corresponding to SEQ ID NOs: 7-8 is Cysteine.

5. The Fc binding protein of claim 1, wherein at least one domain comprises an amino acid sequence selected from the group of SEQ ID NOs: 17-86, 90-95, or an amino acid sequence with at least 89.5% identity thereto, respectively.

6. The Fc binding protein of claim 1, wherein said domain has a deletion of 1, 2, or 3 amino acids within the first 4 amino acids of its N-terminus and/or a deletion of 1 or 2 amino acids within the first 2 amino acids of its C-terminus.

7. The Fc binding protein of claim 1, wherein the protein comprises 2, 3, 4, 5, 6, 7, or 8 domains linked to each other.

8. The Fc binding protein of claim 7, wherein the protein is a homo-multimer or a hetero-multimer.

9. The Fc binding protein of claim 8, wherein one or more domains are linked to each other directly or with one or more linkers.

10. The Fc binding protein of claim 1, wherein the protein is conjugated to a solid support.

11. The Fc binding protein of claim 1, wherein said protein binds to IgG1, IgG2, IgG4, IgM, IgA, Ig fragments comprising the Fc region, fusion proteins comprising an Fc region of an Ig, and conjugates comprising an Fc region of an Ig.

12. An affinity separation matrix comprising the Fc binding protein of claim 1.

13. A method of affinity purification of a protein comprising an Fc sequence, the method comprising: (a) providing a liquid that contains protein comprising an Fc sequence; (b) providing an affinity separation matrix comprising at least one Fc binding protein of claim 1 coupled to said affinity separation matrix; (c) contacting said affinity separation matrix with the liquid under conditions that permit binding of the at least one Fc binding protein of claim 1 to a protein comprising an Fc sequence; and (d) eluting said protein comprising an Fc sequence from said affinity purification matrix.

14. The Fc binding protein of claim 9, wherein one or more domains are linked to each other directly or with one or more peptide linkers.

15. The Fc binding protein of claim 10, wherein the protein is conjugated to a solid support via the Cysteine in position 43, 46, 47, 50, 51, or 53.

* * * * *